(12) United States Patent
Olson

(10) Patent No.: US 7,751,874 B2
(45) Date of Patent: Jul. 6, 2010

(54) DISPLAY FOR ECG DIAGNOSTICS

(76) Inventor: Charles Olson, 43 Lewis Ct., Huntington Station, NY (US) 11746

( * ) Notice: Subject to any disclaimer, the term of this patent is extended or adjusted under 35 U.S.C. 154(b) by 1013 days.

(21) Appl. No.: 11/411,365

(22) Filed: Apr. 25, 2006

(65) Prior Publication Data
US 2006/0258947 A1    Nov. 16, 2006

Related U.S. Application Data

(60) Provisional application No. 60/674,789, filed on Apr. 25, 2005.

(51) Int. Cl.
*A61B 5/04*  (2006.01)
*A61B 5/044*  (2006.01)
(52) U.S. Cl. .................. 600/512; 600/523; 600/525
(58) Field of Classification Search .............. 600/512, 600/523, 525
See application file for complete search history.

(56) References Cited

U.S. PATENT DOCUMENTS

| | | |
|---|---|---|
| 3,186,403 A | 6/1965 | Bassett |
| 3,333,580 A | 8/1967 | Fawcett |
| 3,710,174 A | 1/1973 | Cerniglia, Jr. |
| 3,816,849 A | 6/1974 | Kinoshita et al. |
| 4,136,690 A | 1/1979 | Anderson et al. |
| 4,175,337 A | 11/1979 | Benjo |
| 4,292,977 A | 10/1981 | Krause et al. |
| 4,478,223 A | 10/1984 | Allor |
| 4,528,988 A | 7/1985 | Wong |
| 4,537,202 A | 8/1985 | Mancini et al. |
| 4,587,976 A | 5/1986 | Schmid et al. |
| 4,697,597 A | 10/1987 | Sanz et al. |
| 4,700,712 A | 10/1987 | Schmid |
| 4,850,370 A | 7/1989 | Dower |
| 4,898,181 A | 2/1990 | Kessler |
| 4,922,920 A | 5/1990 | Thie et al. |

(Continued)

FOREIGN PATENT DOCUMENTS

SU    1526645 A1    12/1989

OTHER PUBLICATIONS

Clifton, III et al., "Direct Volume Display Devices", IEEE Computer Graphics & Applications, Jul. 1993.

(Continued)

*Primary Examiner*—Carl H Layno
*Assistant Examiner*—Natasha N Patel
(74) *Attorney, Agent, or Firm*—Carter, DeLuca, Farrell & Schmidt, LLP

(57) ABSTRACT

A medical display for analyzing heart signals includes a cardiographic display which displays an electrocardiograph (ECG) heart signal segment of a patient having a magnitude and location in vector format within a single three-dimensional (3D) coordinate system (vectorcardiograph) sampled at incremental time intervals. The display communicates with a central processing unit (CPU) that implements an algorithm to permit a user to selectively and visually display a comparison of the patient ECG with at least one known display in vector format within a single three-dimensional (3D) coordinate system. The display also permits a user to selectively and visually convert and display an ECG heart signal segment into a color-coded projection of a time sequence, A method for analyzing heart signals includes implementing the algorithm to selectively and visually compare the ECG heart signal with at least one known display in vector format selected from the group.

24 Claims, 20 Drawing Sheets

U.S. PATENT DOCUMENTS

| | | | |
|---|---|---|---|
| 4,949,725 A | | 8/1990 | Raviv et al. |
| 5,046,504 A | | 9/1991 | Albert et al. |
| 5,101,833 A | | 4/1992 | Schmid |
| 5,284,152 A | | 2/1994 | Portnuff et al. |
| 5,458,116 A | | 10/1995 | Eger |
| 5,803,084 A | * | 9/1998 | Olson .................. 600/512 |
| 6,226,542 B1 | | 5/2001 | Reisfeld |
| 6,226,543 B1 | | 5/2001 | Gilboa et al. |
| 6,230,048 B1 | * | 5/2001 | Selvester et al. .......... 600/523 |
| 6,301,496 B1 | | 10/2001 | Reisfeld |
| 6,385,476 B1 | | 5/2002 | Osadchy et al. |
| 6,438,409 B1 | | 8/2002 | Malik et al. |
| 6,456,867 B2 | | 9/2002 | Reisfeld |
| 6,546,271 B1 | | 4/2003 | Reisfeld |
| 6,694,178 B1 | | 2/2004 | Soula et al. |
| 6,721,593 B2 | | 4/2004 | Anderson et al. |
| 6,754,523 B2 | | 6/2004 | Toole |
| 6,884,218 B2 | | 4/2005 | Olson |
| 6,920,350 B2 | | 7/2005 | Xue et al. |
| 6,937,899 B2 | | 8/2005 | Sheldon et al. |
| 7,010,349 B2 | | 3/2006 | Conley et al. |
| 2003/0028119 A1 | | 2/2003 | Xue et al. |
| 2003/0045805 A1 | | 3/2003 | Sheldon et al. |
| 2004/0111021 A1 | | 6/2004 | Olson |
| 2004/0116982 A1 | | 6/2004 | Conley et al. |

OTHER PUBLICATIONS

Te-Chuan Chou et al., "Clinical Vectorcardiography": Foreword (2 pages); "Section I—Chapter 1—The Vector Concept" Fig. 1.1; Fig. 1.2 (2 pages); Fig. 5.3—Mean values of various measurements of QRS and Tloops—Grune & Stratton, Inc., New York and London, 1967.

Rob MacLeod et al. "Report of the first visualization of the reconstructed electrocardiographic display symposium" Journal of Electrocardiology Table of Contents; ECG Imaging—p. 385 Abstract; "Fig. 3-Tenmillisecond images of normal activation in a normal human heart . . . "; vol. 38, No. 4, Oct. 2005.

Charles W. Olson "The Overlooked Utility of a 3D Cardiographic Display". 6 pages, U.S. Copyright Office registration TXU 913-733. Aug. 16, 1999 (2 pages).

Charles W. Olson "A New 3D Vector Cardiograph" 10 pages, U.S. Copyright Office registration TXu 913-345, Aug. 16, 1999 (2 pages).

Charles W. Olson "3D Vectorcardiographic Display" pp. 1-25, 86-111, U.S. Copyright Office registration TXu 913 732. Aug. 16, 1999 (2 pages).

Charles W. Olson "3D Vector Cardiographic Display Training Program" pp. 1-25, 139-164, U.S. Copyright Office registration TXu-1-102-488, May 12, 2003 (2 pages).

Charles W. Olson "T-Wave Analysis" First 25 pages, Last 25 pages U.S. Copyright Office Registration TXu 1-150-475 Dec. 17, 2003 (2 pages).

* cited by examiner

Statistics of Critical Measurements
Measurement                      Value    Zscore Maximum QRS Ampl.            .966 mv    -1.07
Duration in ms                 84 ms    -0.33
Azimuth Angle at max          -39 deg   -0.84
Elevation Ang.at max           40 deg    1.17
Narrowness of Vectgr.        1.06        1.78
Initial Azimuth Ang.           28 deg   -0.25
Initial Elevat. Ang.           21 deg    0.61
T-Wave Max. Ampl.            .235 mv    -1.08
T-Wave Azimuth at Max          60 deg    0.32
T-Wave Elevat. at Max           0 deg   -1.50

⎫
⎬ 66
⎭

Probable Patient Diagnosis: ← 30
Norm: Norm

Heart Rate    = 60 BPM          ← 70
PR Interval   = 140 millisec.
QRS Duration  = 90 millisec
QT Interval   = 434 millisec

FIG. 5

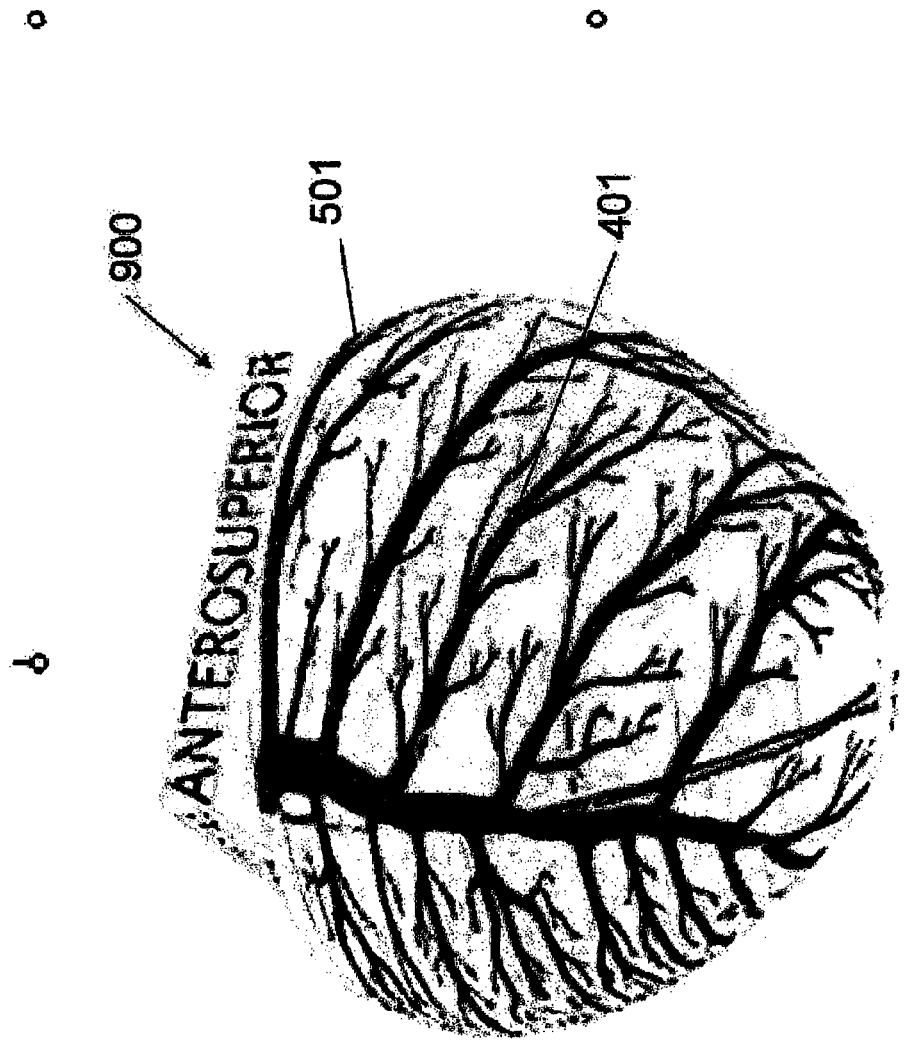

DISPLAY FOR ECG DIAGNOSTICS

CROSS-REFERENCE TO RELATED APPLICATIONS

This application claims the benefit of priority under 35 U.S.C. §119 of U.S. Provisional Patent Application Ser. No. 60/674,789 by Olson entitled "DISPLAY FOR ECG DIAGNOSTICS" filed on Apr. 25, 2005, the entire contents of which are incorporated by reference herein.

BACKGROUND

1. Technical Field

The present disclosure relates to a diagnostic display for an electrocardiograph (ECG).

2. Related Prior Art

Three-dimensional (3D) electronic presentation of clinical ECG interpretations are known in the art. Increasingly, physicians are performing clinical ECG interpretations electronically. The change from paper to electronic presentation provides the potential for the physician to receive such immediate decision support as the required educational software is developed. This might appropriately be considered as receiving a self-guided "second opinion" regarding a clinical decision.

However, when physicians are uncertain whether to accept or alter automated diagnostic statements, there is no immediately available support for their decision.

SUMMARY

The present disclosure relates to a medical display for analyzing heart signals, that includes a cardiographic display which displays at least a segment of an, or an entire, electrocardiograph (ECG) heart signal of a patient having a magnitude and location in vector format within a single three-dimensional (3D) coordinate system, e.g., X, Y, Z, (vectorcardiograph) sampled at incremental time intervals. The display operatively communicates with a central processing unit (CPU) that implements a diagnostic algorithm to permit a user to selectively and visually display a comparison of the at least a segment of the patient ECG signal with at least one known display in vector format within a single three-dimensional (3D) coordinate system. The known display(s) consist of a normal cardiac condition (including a patient's prior or current normal condition) or an abnormal or reference cardiac condition that includes at least one of a patient prior or current cardiac condition, a myocardial infarction condition, a hypertrophic condition, an ischemic condition, and a bundle branch block condition. The known displays in vector format are stored in a known cardiac conditions database, which in turn is stored in a memory operatively coupled to the CPU. The cardiographic display operatively communicates with the CPU to allow a user to selectively display critical measurements of at least one of the at least a segment of the patient ECG signal, obtained via patient monitoring, and the known display(s) in vector format.

The algorithm may compare the patient ECG critical measurements to the critical measurements stored in the cardiac conditions database and the CPU may operatively communicate with the cardiographic display to visually display the results of the comparison as a normal or abnormal condition. In addition, the cardiographic display may operatively communicate with the CPU to allow a user to selectively display an overlay over the vectorcardiograph patient ECG, with the overlay including at least one of a 3D representation of a heart, a representation of coronary arteries over a projection of a heart, and a 3D vectorcardiograph of a cardiac condition. The at least a segment of the patient ECG signal includes at least one of a P-wave interval, PR interval, QRS interval, QT interval and T-wave interval.

The present disclosure relates also to a medical display for analyzing heart signals, which includes a cardiographic display which displays at least a segment of an electrocardiograph (ECG) heart signal of a patient having a magnitude and location in vector format within a single three-dimensional (3D) coordinate system (vectorcardiograph) sampled at incremental time intervals. The display operatively communicates with a central processing unit (CPU) that implements an algorithm to permit a user to selectively and visually convert and display the at least a segment of the patient ECG into at least a first color coded projection of a time sequence of the at least a segment of an ECG heart signal. The color coded time sequence projection corresponds to a lead signal associated with the magnitude and location of the vector signal. The color coded time sequence represents a time line duration of the vector signal.

The present disclosure relates also to a method for analyzing heart signals, which includes the step of implementing the algorithm to permit a user to selectively and visually display a comparison of the electrocardiograph (ECG) heart signal of a patient having a magnitude and location in vector format within a single three-dimensional (3D) coordinate system (vectorcardiograph) sampled at incremental time intervals with at least one known display in vector format within a single three-dimensional (3D) coordinate system. The known display(s) consist of a normal cardiac condition (including a patient's prior or current normal condition) or an abnormal or reference cardiac condition that includes at least one of a patient prior or current cardiac condition, a myocardial infarction condition, a hypertrophic condition, an ischemic condition, and a bundle branch block condition. As previously indicated, the known displays in vector format are stored in the known cardiac conditions database, which in turn is stored in the memory.

The step of implementing the algorithm may further include implementing the algorithm to allow the user to selectively display the critical measurements of at least one of the patient ECG and the known display in vector format. The step of implementing the algorithm further may also include implementing the algorithm to allow a user to compare the patient ECG critical measurements to critical measurements stored in a database and to operatively communicate with the cardiographic display to visually display the results as a normal or abnormal condition. The step of implementing the algorithm may further include implementing the algorithm to allow a user to selectively display an overlay over the vectorcardiograph patient ECG. The overlay includes at least one of a 3D representation of a heart, a representation of coronary arteries over a projection of a heart, and a 3D vectorcardiograph of a cardiac condition. The at least one segment of a patient ECG signal includes at least one of a P-wave interval, PR interval, QRS interval, QT interval and T-wave interval.

The present disclosure relates also to a method for analyzing heart signals which includes the step of implementing an algorithm to permit a user to selectively and visually convert and display at least a segment of an ECG into a color coded projection of a time sequence of the at least a segment of an ECG heart signal. The color coded time sequence projection corresponds to a lead signal associated with the magnitude and location of the vector signal. The color coded time sequence represents a time line duration of the vector signal.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The subject matter regarded as the embodiments is particularly pointed out and distinctly claimed in the concluding portion of the specification. The embodiments, however, both as to organization and method of operation, together with objects, features, and advantages thereof, may best be understood by reference to the following detailed description when read with the accompanying drawings, wherein similar reference characters denote similar elements throughout the several views, in which:

FIG. 5 illustrates the statistics of critical parameters compared to a normal heart as found in 50 patients having a catheter verification of normality; and includes an enlarged view of the data on the right-side of the display of FIG. 1;

FIG. 19 illustrates a 3D overlay of the coronary arteries of the heart superimposed on a heart.

DETAILED DESCRIPTION

U.S. Pat. No. 5,803,084 by Olson, issued Sep. 8, 1998, entitled "THREE DIMENSIONAL VECTOR CARDIOGRAPHIC DISPLAY AND METHOD FOR DISPLAYING SAME" and U.S. Pat. No. 6,884,218 B2 by Olson, issued Apr. 26, 2005, entitled "THREE DIMENSIONAL VECTOR CARDIOGRAPH AND METHOD FOR DETECTING AND MONITORING ISCHEMIC EVENTS" are incorporated by reference herein in their entirety.

Figure 1:
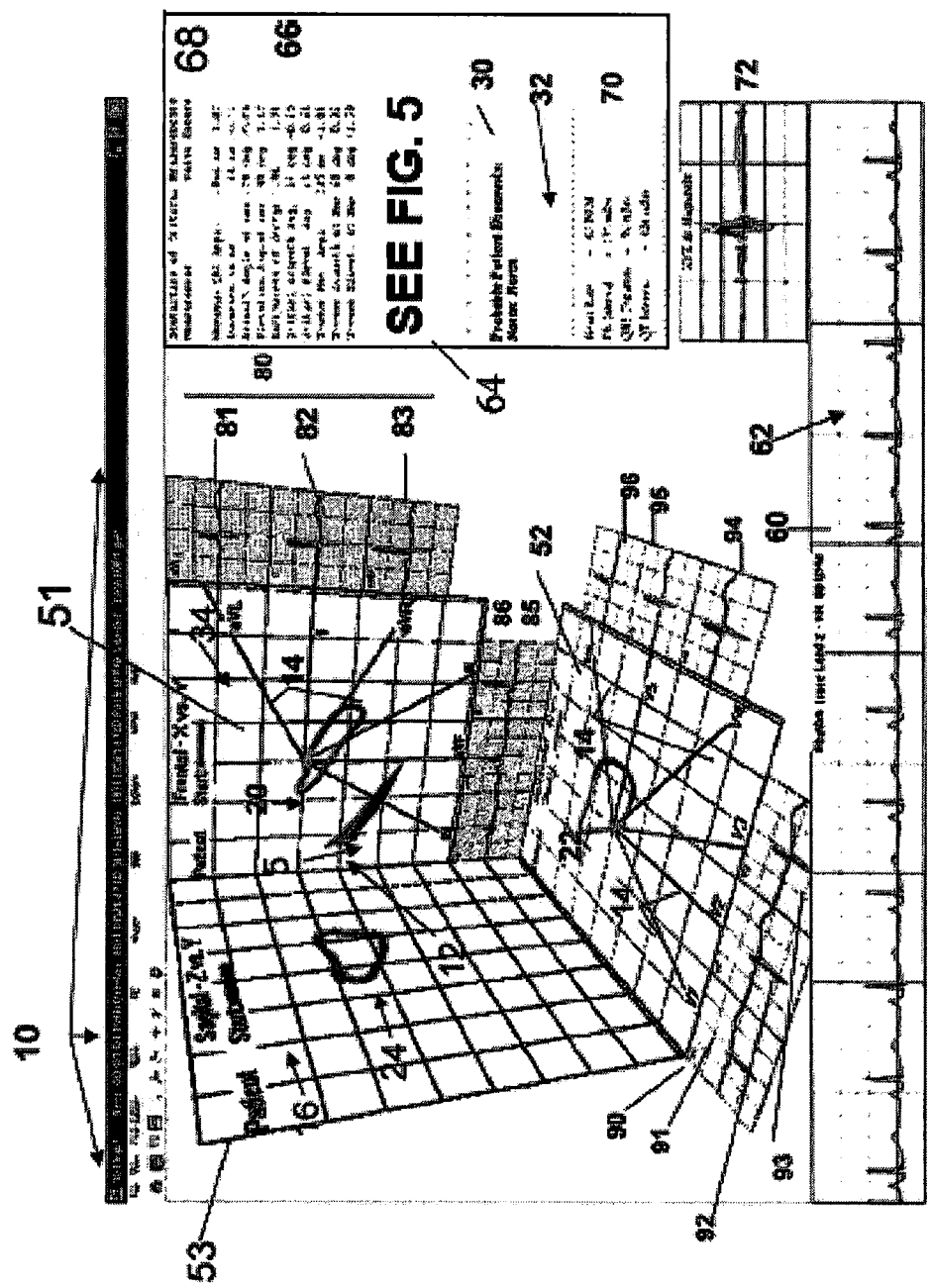
FIG. 1 illustrates a first operating display of a patient file in a 3D vectorcardiograph in which patient files are selected from a file menu box according to a method of the present disclosure for displaying an ECG signal.

FIG. 1 illustrates a medical display or cardiographic diagnostic display 10 for displaying at least one segment of, or an entire, electrocardiograph (ECG) heart signal 12 having a magnitude and location in vector format within a single three-dimensional (3D) coordinate system (e.g., X, Y, Z as shown) which is sampled at incremental time intervals according to the present disclosure. More particularly, the display 10 displays and separates cardiac conditions into recognizable patterns of 3D vectors 14. The segments of the ECG signal 12 vector patterns may include a P-wave segment, a QRS segment, or a T-wave vector segment or combinations thereof. However, for illustrative purposes only, FIGS. 1, 2, 8-13, and 15-16 display a QRS segment or portion of a lead signal. As described below with respect to FIGS. 17-18, a color code map is used to identify the time sequence of the lead vectors 14. The display 10 is a top level display which may be utilized for making a substantially immediate probable diagnosis 30. The probable diagnosis 30 is shown in right middle region 32 of the display 10. The probable diagnosis 30 is determined as a result of implementation of a machine algorithm as discussed below with respect to FIG. 3. In a large area 34, a 3D picture of the ECG of the patients' heart 5 is shown with planar projections or vector loops 20, 22 and 24 projected as time sequences, in color-coded form, into the three planes: Frontal 51, Horizontal 52 and Sagital 53, respectively, as first color-coded projections. The lead vectors 14 include vector lead aVL, vector lead 1, vector lead aVR, vector lead II, vector lead aVF, and lead vector III associated with the frontal plane 51, and vector lead V1, vector lead V2, vector lead V3, vector lead V4, vector lead V5 and vector lead V6 associated with the horizontal plane 52.

The first color-coded frontal planar projection or vector loop 20 in turn is projected into lead projections as second color-coded projection 81 corresponding to vector lead aVL, second color-coded projection 82 corresponding to vector lead I, and second color-coded projection 83 corresponding to vector lead aVR, the foregoing each displayed on a vertical side panel 80 associated with frontal plane 51, and also as second color-coded projection 86 corresponding to vector lead II, second color-coded projection 87 corresponding to vector lead aVF, and second color-coded projection 88 corresponding to vector lead III, the foregoing each displayed on a vertical lower panel 85 associated with frontal plane 51.

The first color-coded frontal planar projection or vector loop 22 in turn is projected into lead projections as second color-coded projection 91 corresponding to vector lead V1, second color-coded projection 92 corresponding to vector lead V2, and second color-coded projection 93 corresponding to vector lead V3, the foregoing each displayed on a horizontal panel 90 associated with horizontal plane 52, and also as second color-coded projection 94 corresponding to vector lead V4, second color-coded projection 95 corresponding to vector lead V5, and second color-coded projection 96 corresponding to vector lead V6, the foregoing each displayed on a horizontal panel 98 associated with horizontal plane 52.

Although those skilled in the art recognize the character of a normal heart in the form of the 3D picture 5, as discussed below with respect to FIGS. 12 and 14, a 3D picture of a wide variety of disease states can be over laid to facilitate and enhance diagnosis. As defined herein, an overlay is construed as, but not limited to, the following examples: a top over a bottom view, a dual screen or side by side illustration, or a phantom illustration. The embodiments are not limited in this context.

As further confirmation of the result, a chart of statistical information 66 is shown in upper right region 68. The chart of statistical information 66 itemizes the critical parameters of the 3D measurement and presents the corresponding Z-scores. Lower region 62 of the display 10 may include a rhythm strip 60 which provides additional information relating to rhythmic types of abnormalities. Also projections onto the 12 Leads are shown.

The 3D image of the heart 5 and the surrounding background in 3D can be rotated and expanded to view any part of the image of the heart 5 in greater detail.

Figure 2:
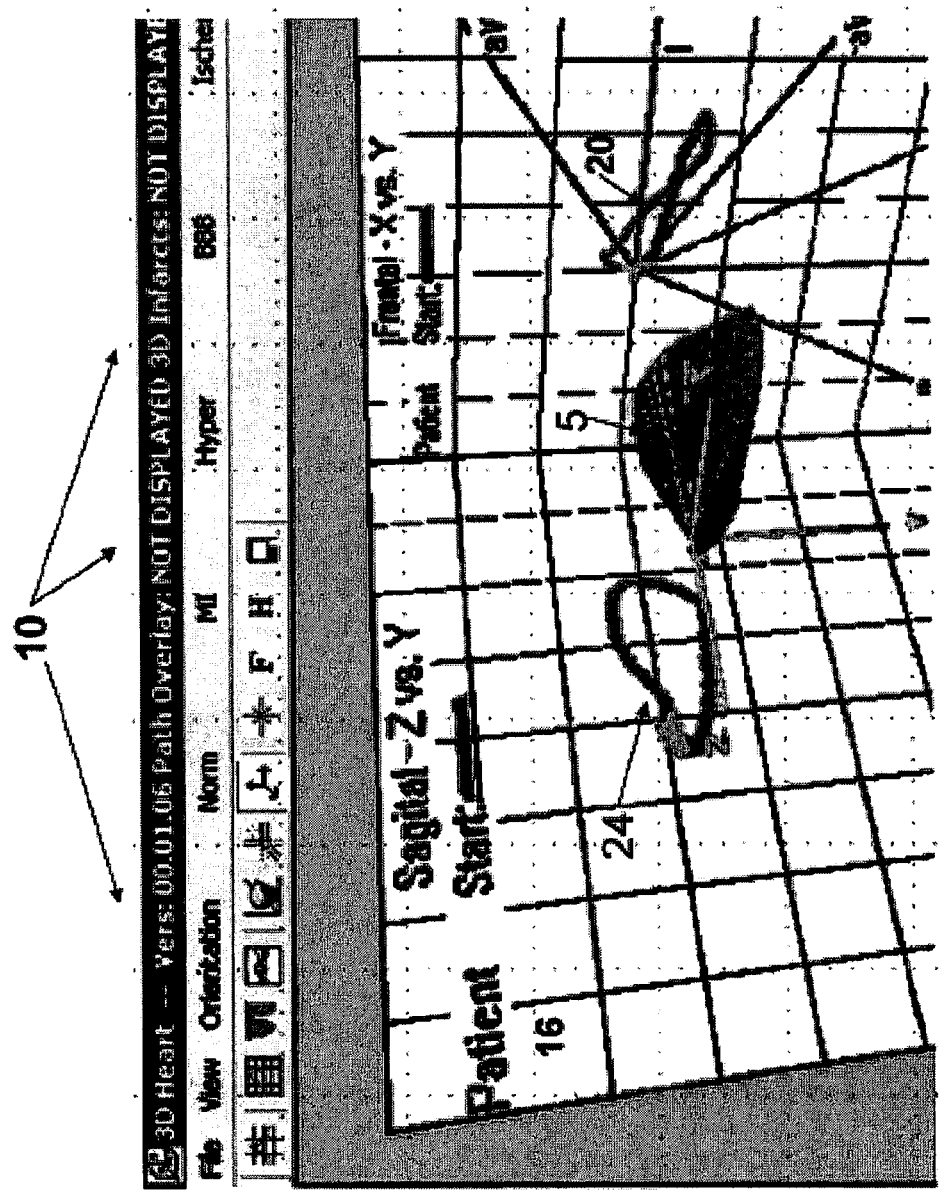
FIG. 2 illustrates an expansion of the upper left portion of the initial display showing a frontal and sagital projection of a 3D vector diagram seen at the origin of the display.

FIG. 2 illustrates an expansion of upper left portion 16 of the initial display 10 showing a frontal and sagital projection of the 3D vector diagram 12. The origin of the ECG vectorcardiograph signal display 12 is the intersection of X, Y and Z axes, i.e., at the origin of the X, Y, and Z axes.

Figure 3:
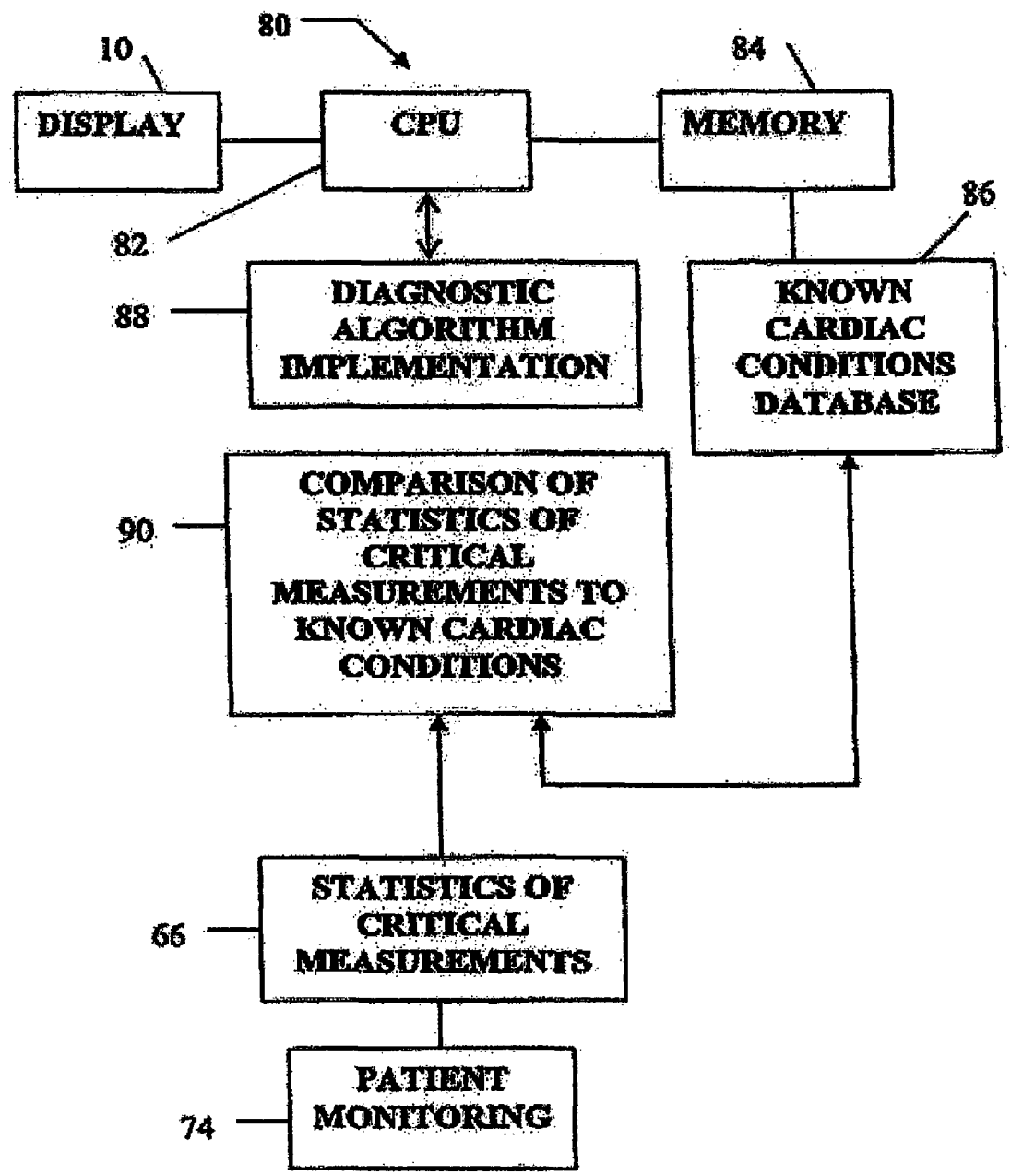
FIG. 3 illustrates a schematic diagram of a medical display system according to the present disclosure.

FIG. 3 is a schematic diagram of a medical display system and method 80 according to the present disclosure. More particularly, a central processing unit (CPU) 82 is operatively coupled to the display 10 and to a memory 84. The memory 84 stores a known cardiac conditions database 86. The CPU 82 implements a diagnostic algorithm 88 causing a comparison 90 of the statistics of critical measurements 66 to the known cardiac conditions stored in the known cardiac conditions database 86. The statistics of critical measurements 66 are derived from patient monitoring 74, in which the actual patient cardiac measurements are operatively communicated to the CPU 82 during the steps of comparing 90 to the known cardiac conditions in the database 86 resulting from the implementation 88 of the diagnostic algorithm.

Figure 4A:
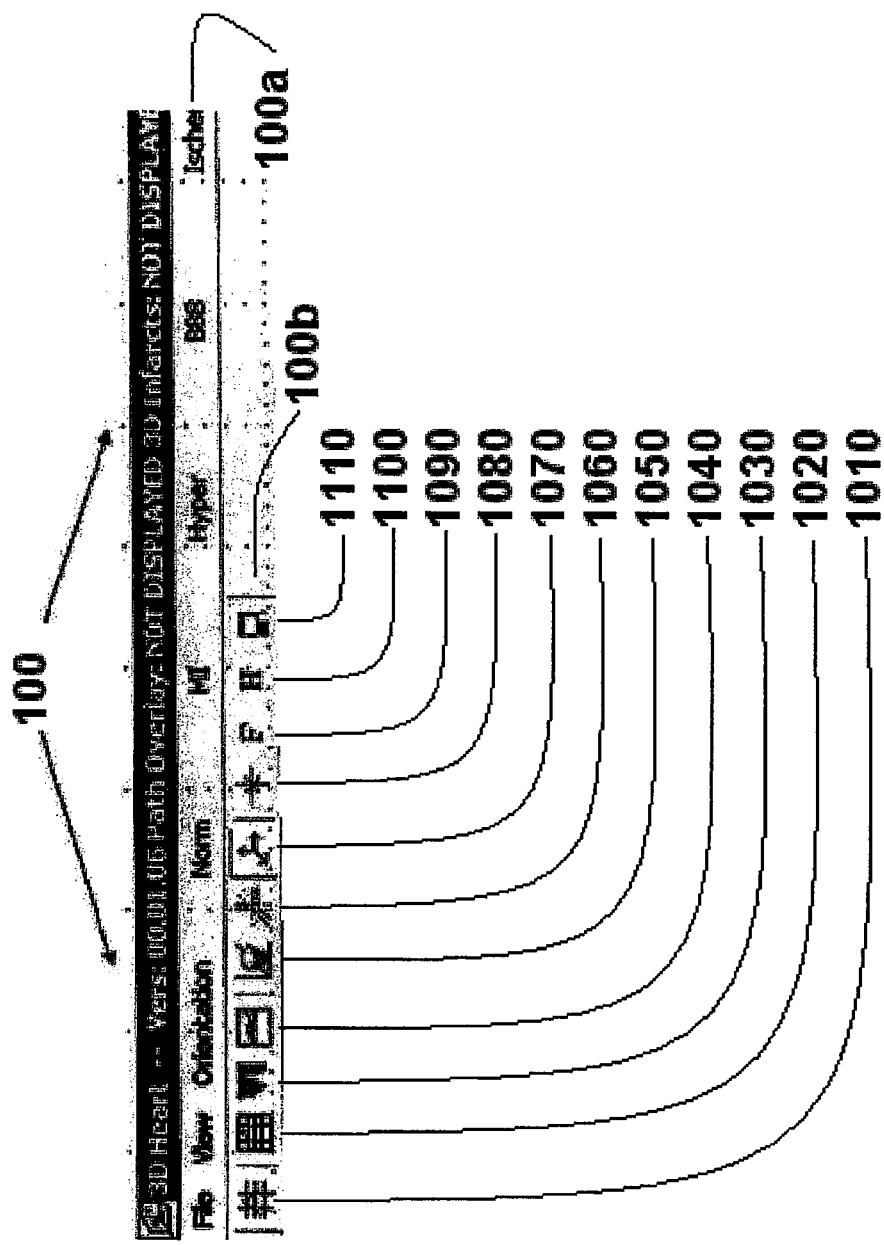
FIG. 4A is a detailed view of the display of FIG. 1 illustrating specific tool bar functions of the display.
Figure 4B:
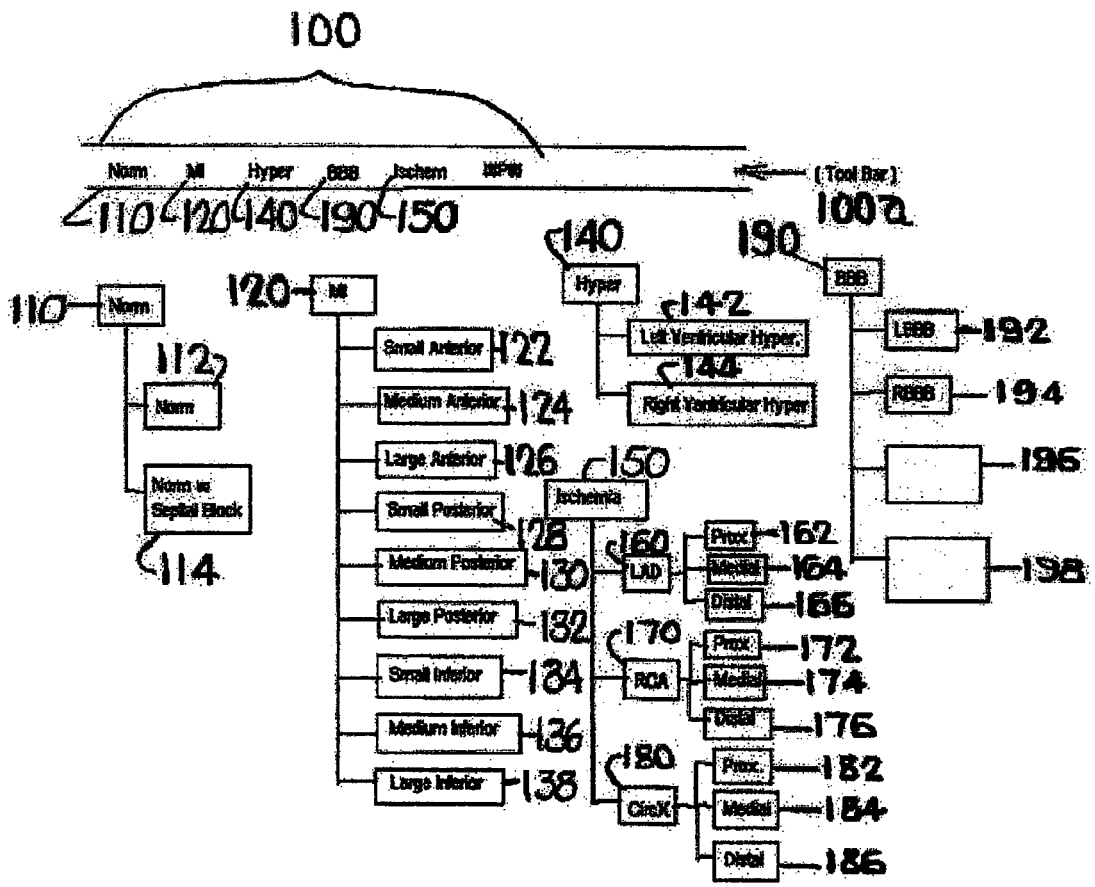
FIG. 4B illustrates tool bar selections of disease states of the general population for comparison with a patient's ECG.

Referring to FIGS. 4A and 4B, FIG. 4A is a detailed view of the display 10 illustrating specific tool bar functions of the display 10. More particularly, the display 10 includes a first toolbar 100a having a group of selections 100 which includes cardiac conditions 102 (see FIG. 4B). In addition, the selections 100 include cardiac condition 155 which represents Wolfe-Parkinson-White Syndrome.

A second toolbar 100b includes a series of icons. As illustrated by way of example in FIG. 4A, from left to right, a first icon 1010 represents a command to open a patient file for input. A second icon 1020 represents the selection of normal 12 lead ECG display. A third icon 1030 represents a mercator projection command. A fourth icon 1040 represents the display of a full ECG heart beat showing P-wave, QRS, and T-wave with fiducial bars to show the start and end of these waves. A fifth icon 1050 superimposes or overlays an image of the heart 5 over the 3D vector diagram 12. A sixth icon 1060 represents an overlay command of a version of the 3D ECG associated with the particular disease or cardiac condition 100 chosen. A seventh icon 1070 represents an X, Y, Z coordinates command. An eighth icon 1080 resets the display 10 to a default orientation. A ninth icon represents a frontal plane "F" command. A tenth icon 1090 represents a horizontal plane "H" command. Finally, an eleventh icon 1100 represents a command to save the present orientation. Other icons may be added as desired.

FIG. 4B illustrates the tool bar selections 100 of the cardiac conditions 102 of the general population for comparison with an ECG 12 of a patient. For comparison purposes, the cardiac conditions 102 include normal conditions 110. The normal conditions 110 are sub-divided into entirely normal states 112 and normal states with septal blockage 114.

The cardiac conditions 102 selectable by the tool bar 100 also include myocardial infarctions (MI) 120 which are sub-categorized into small, medium and large anterior states 122, 124 and 126, respectively; small, medium and large posterior states 128, 130 and 132, respectively; and small, medium and large interior states 134, 136 and 138, respectively.

The cardiac conditions 102 also include hypertrophy 140 which is sub-categorized into left ventricular hypertrophy 142 and right ventricular hypertrophy 144. In addition, ischemia conditions 150 are sub-divided into three major sub-divisions: left anterior descending (LAD) 160; right coronary artery (RCA) 170; and circumflex (CircX) 180. The sub-division LAD 160 is sub-categorized into proximal, medial and distal 162, 164, and 166, respectively. Similarly, the sub-division RCA 170 is also sub-categorized into proximal, medial and distal 172, 174, and 176, respectively. As well, the sub-division CircX 180 is sub-categorized into proximal, medial and distal 182, 184, and 186, respectively.

Finally, the cardiac conditions 102 also include bundle branch block (BBB) states 190 which are sub-categorized into: left bundle branch block (LBBB) 192; right bundle branch block (RBBB) 194; left posterior fascicular block 196 and left anterior fascicular block 198.

The tool bar selections 100 provide drop menus of a wide variety of cardiac condition disease states 102 that can be used for comparison with the ECG of a patient. The 3D ECG of the disease state chosen is over laid on top of the patient's 3D ECG for a simple and rapid comparison.

Therefore, the tool bar selections 100 on the display 10 enable display of at least two of the cardiac conditions 102, e.g., the normal cardiac conditions 110, the myocardial infarction (MI) condition 120, the hypertrophy conditions 140, the ischemic conditions 150, and the bundle branch block (BBB) conditions 190.

The user, such as a doctor, may display the critical measurements 66 of at least one of the recognizable patterns of 3D vectors 14. The user may compare the display of critical measurements 66 to statistical information for at least one of the cardiac conditions 102. The cardiac condition 102 may include an abnormality such as the myocardial infarction (MI) condition 120, the hypertrophy conditions 140, the ischemic conditions 150, and the bundle branch block (BBB) conditions 190.

FIG. 5 is an enlarged view of the right side panel of information 64 of FIG. 1 and illustrates the statistics of critical parameters or measurements 66 compared to a normal heart as found in 50 patients having a catheter verification of normality. The right side of the display shows the Statistics of Critical Measurements 66. The measured value for the patient is shown as the Value. The Zscore is the number of standard deviations of the patient's reading from a normal mean or median value. The Zscore is an example of an important measurement made readily available to a user of the cardiographic diagnostic display 10. As defined herein, a user may be a human such as a doctor or physician, a nurse, or medical technician or other skilled professional or a user may be a machine programmed to perform a diagnostic function by visual observation or selective manipulation of the medical displays or methods described herein. Also illustrated in FIG.

Figure 6:
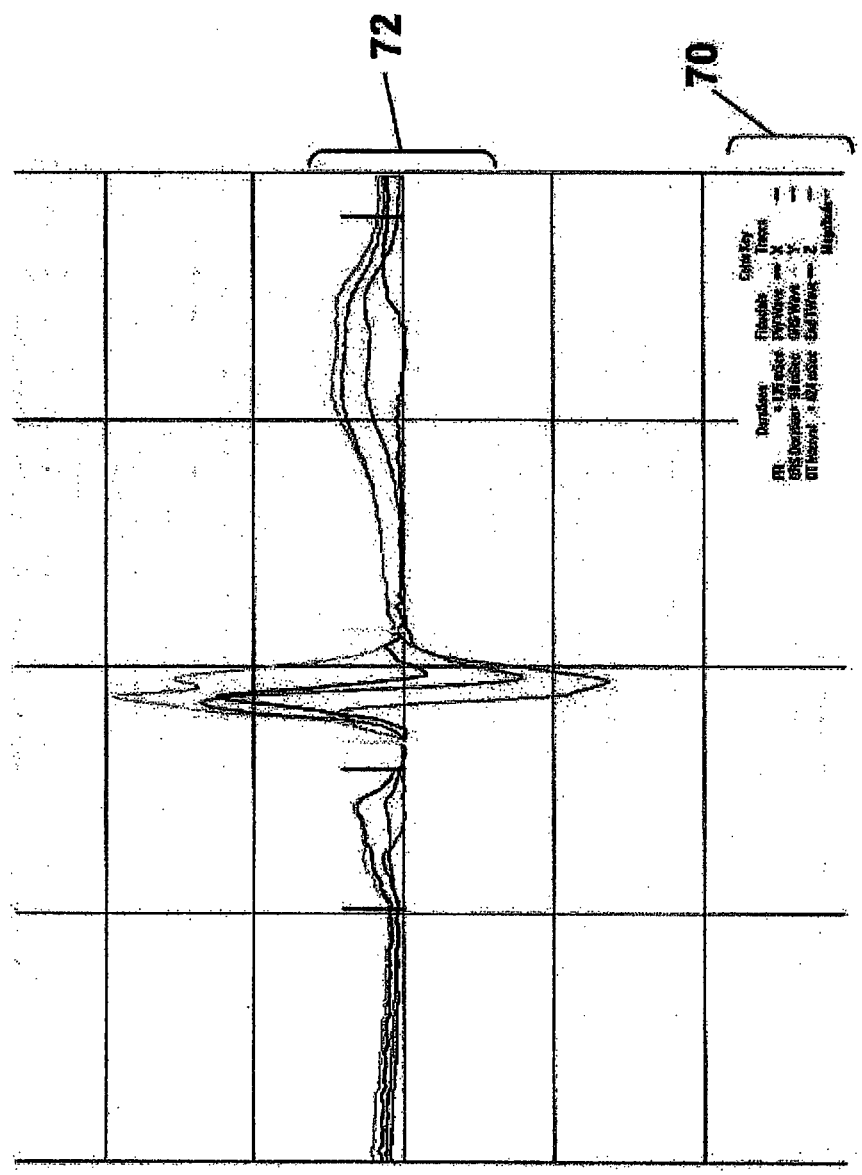
FIG. 6 illustrates the validity of fiducial points that have been automatically selected by a software algorithm according to the present disclosure.

5 are the examples of fiducial points 70 that are displayed in the panel of information 64 in FIG. 1 and also in the lower portion of FIG. 6.

The probable patient diagnosis 30 is shown at the bottom. The Statistics of Critical Measurements 66 may include, but are not limited to, the Maximum QRS Amplitude, the Duration in milliseconds (ms), the Azimuth Angle at maximum, the Elevation Angle at maximum, the Narrowness of width of the 3D vectorgraph compared to the measurement of the QRS amplitude, the Initial Azimuth Angle, the Initial Elevation Angle, the T-wave Maximum Amplitude, T-wave Azimuth at Maximum, T-wave Elevation at Maximum. Other measurements may also be added and may be part of a sub-menu and/or a user-specific display variable.

FIG. 6 illustrates the validity of fiducial points 70 that have been automatically selected by a software algorithm according to the previous disclosure. The important measurements are also shown in this view. The fiducial selections, e.g., PW wave, QRS wave, and the End of the T wave, are shown. Also indicated at the bottom is the PR interval, QRS interval and the QT interval. FIG. 6 is an expanded version of the graphical plot 72 illustrated in the lower right-hand corner of FIG. 1. The expansion of the graphical plot in FIG. 1 can be rapidly selected by clicking on a corresponding symbol or marker on the tool bar 100 display, for example, the symbol icon 1040 illustrated in FIG. 4A.

Figure 7:
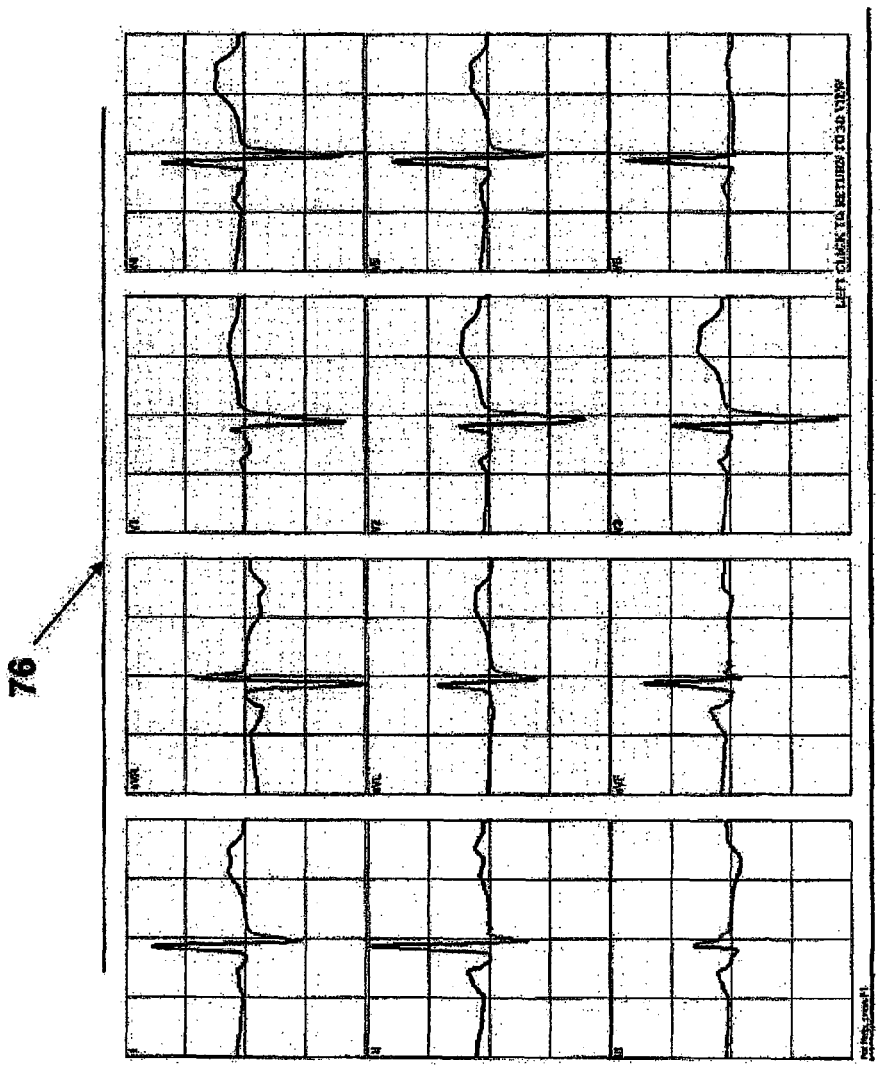
FIG. 7 illustrates a prior art 12 lead ECG display which can be displayed by the method of the present disclosure.

FIG. 7 illustrates a prior art 12 lead ECG display 76. By selecting a second function or sub-menu 1020 of the tool bar 100, a full screen display of patient data may be shown.

Figure 8:
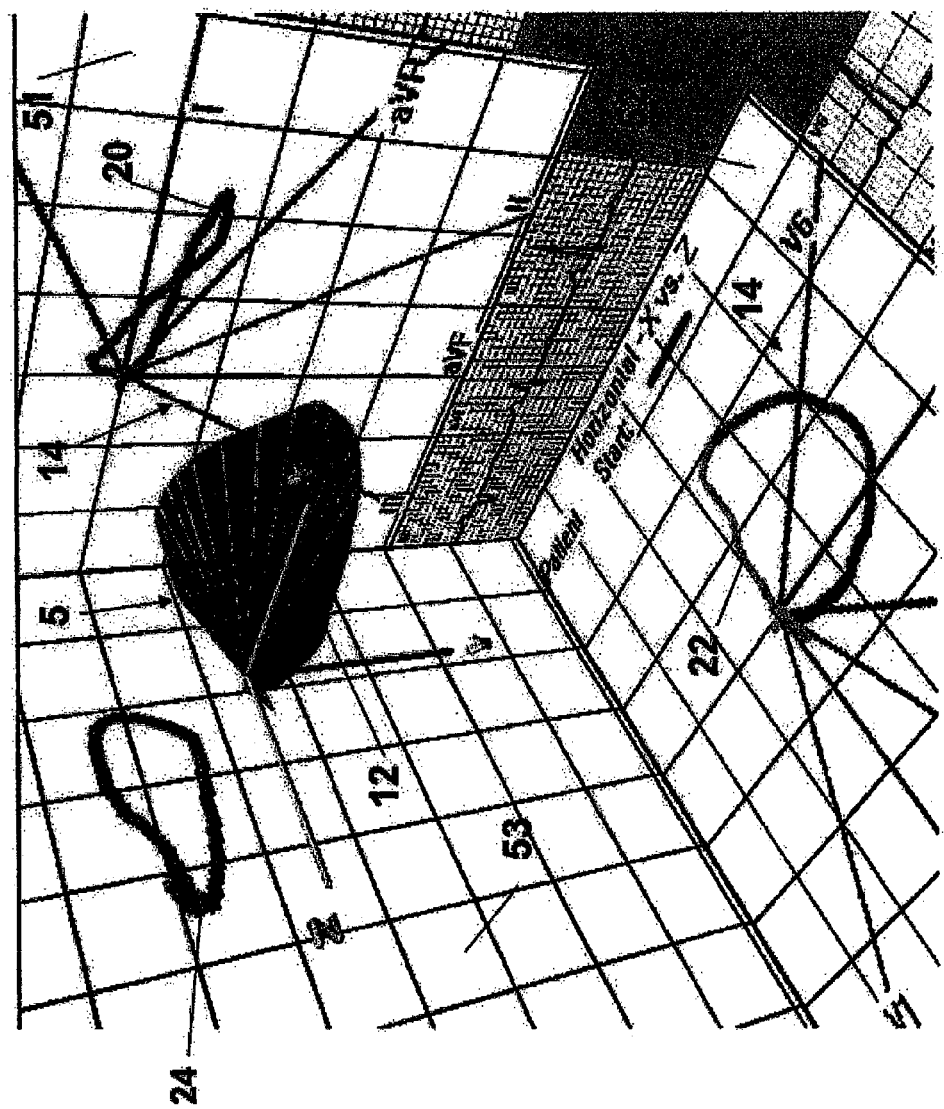
FIG. 8 illustrates an expanded view of the 3D vectorcardiograph of FIG. 1 showing more details.

FIG. 8 illustrates an expanded view of the 3D vectorcardiograph 12 of FIG. 1 showing more details for the same patient illustrated in FIG. 1. The 3D display 10 can be expanded and the display 10 rotated to show more detail of the patient data, and to provide an expanded angle of view. Optional X, Y and Z coordinate axes have been added to the 3D picture 10 to provide orientation of the ECG in the body of the patient (not shown). The X, Y and Z coordinate axes are selected by clicking on a tool bar symbol 1070 or sub-menu (not shown) showing the three axes.

Therefore, the display 10 displays one heart signal as X, Y and Z vector signals and the resultant magnitude of the signal Although an X, Y and Z coordinate system is illustrated in FIG. 8, other coordinate systems such as, but not limited to, cylindrical coordinate systems (e.g., r, $\Theta$, z) or spherical coordinates (e.g., r, $\theta$, $\phi$) may also be applied. The embodiments are not limited in this context.

The X, Y and Z vector signals and the resultant magnitude of the signal are displayed to illustrate an estimate of at least one of P-wave interval, PR interval, QRS interval, QT interval and T-wave interval. For example, the resultant magnitude $Mag_{vd}$ of any signal can be determined by the following formula: $Mag_{vd} = \sqrt{(x^2+y^2+z^2)}$ where x is the magnitude of the X-component of the 3D vectorcardiograph 12, y is the magnitude of the Y-component of the 3D vectorcardiograph 12, and z is the magnitude of the Z-component of the 3D vectorcardiograph 12, or in effect, x, y, and z are the orthogonal coordinates of the 3D vector 12.

Figure 9:
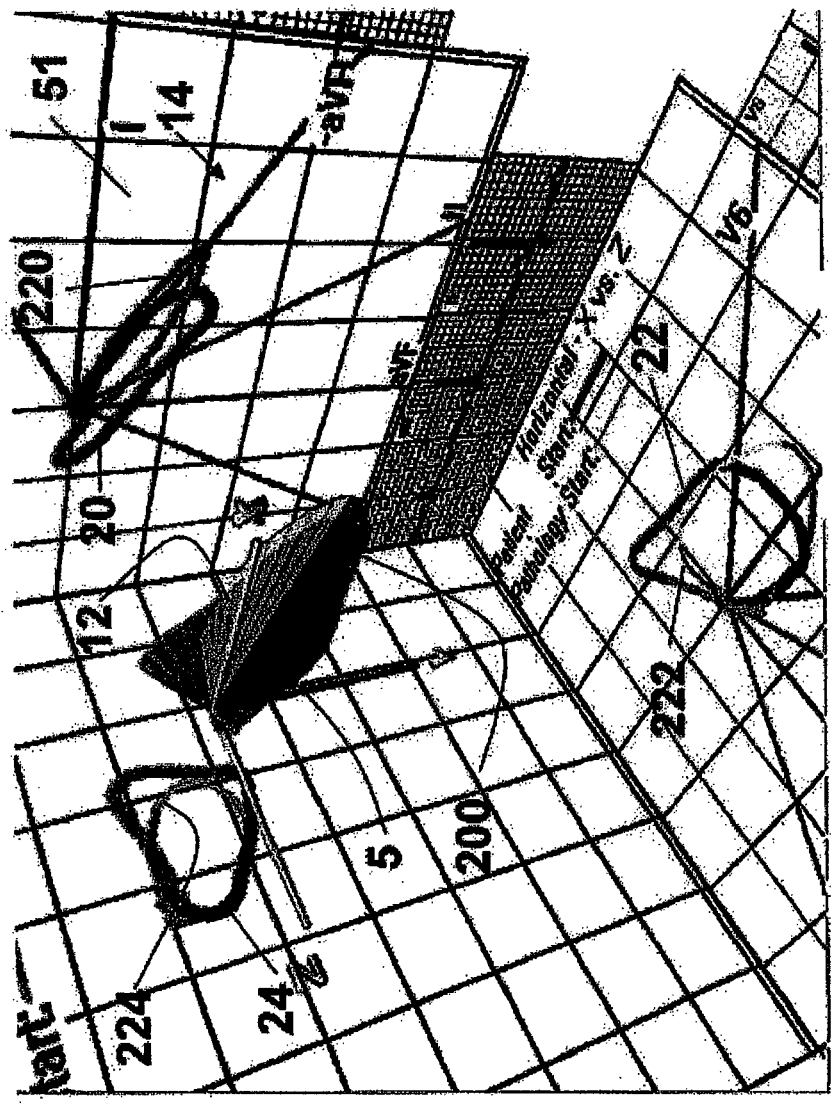
FIG. 9 illustrates an average of the critical parameters of the 50 patients having a normal heart overlaying the 3D vectorcardiograph of FIG. 8.

FIG. 9 illustrates an average 200 of the critical parameters of the 50 patients having a normal heart overlaying the 3D vectorcardiograph 12 of FIG. 8. The average 200 of 50 normals is over laid or compared to the previous patient data 12 both in the 3D display, and the three planes, illustrated as 220, 222 and 224 for the X, Y and Z axes, respectively. The color code for the normal master is light blue, brown, yellow and green. By selecting the tool bar symbol for a given over lay (e.g., icon 1060 in FIG. 4A), the 3D vectorcardiogram of the diagnosed disease is over laid the patient ECG. This is illustrated in, and discussed below with respect to, FIG. 13, which compares a vector cardiogram of a heart of normal patient to that of a heart of a patient having experienced a large anterior myocardial infarction.

FIG. 9 shows the advantages of using 3D patterns for recognizing and diagnosing heart conditions. The average 200 of 50 normal patients is used as a control to compare to the ECG 12 of the patient. Those skilled in the art may quickly and readily perceive a normal heart condition versus any give patient by matching the patient ECG 12 in timing size, duration and in the planar characteristics. The projected signals in the three planes 220, 222 and 224, respectively, may also be used to closely match the normal average 200.

Figure 10:
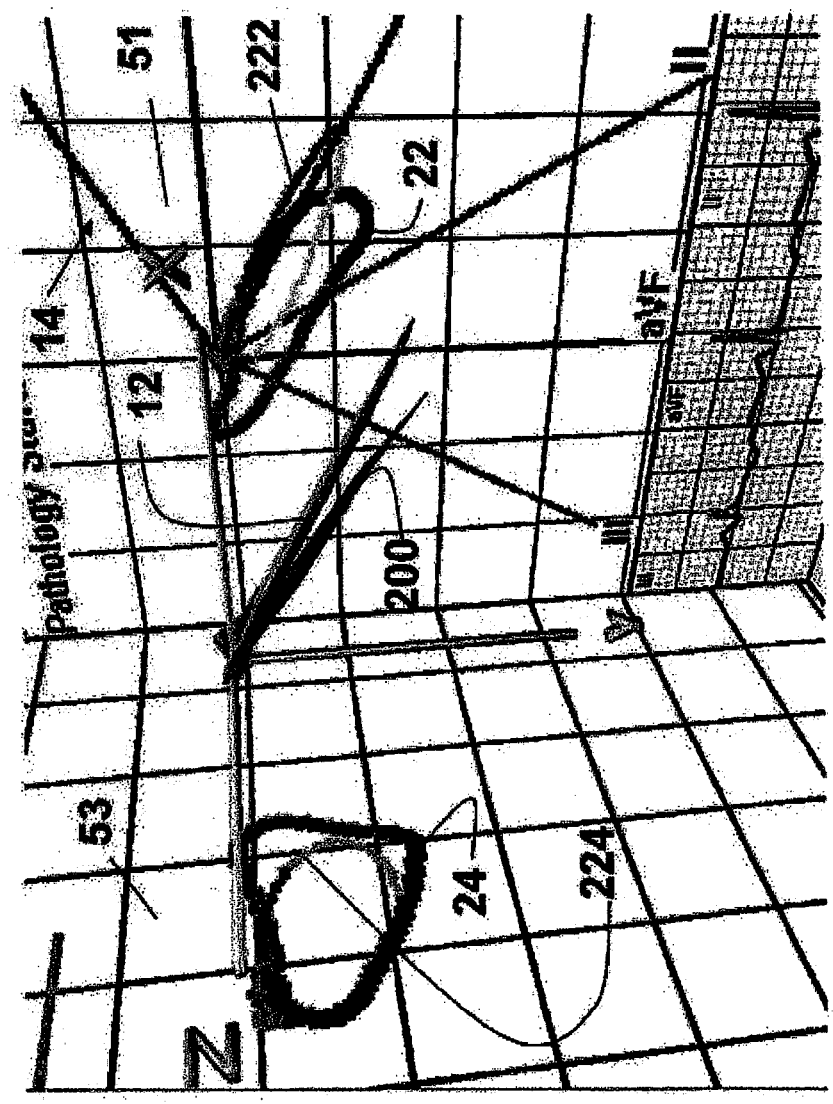
FIG. 10 illustrates a side or edge view of the 3D vectorcardiograph of FIG. 9.

FIG. 10 illustrates a side or edge view of the 3D vectorcardiograph 12 of FIG. 9. This is another view of the previous display of FIG. 9 showing the 3D vectors 200 on edge. Normal heart vectors 12 in many cases, may lie in a single plane, as evident in FIG. 10. Distortion of the planar characteristic of the normal heart vectors 12 is another indicator of a diseased condition.

Figure 11:
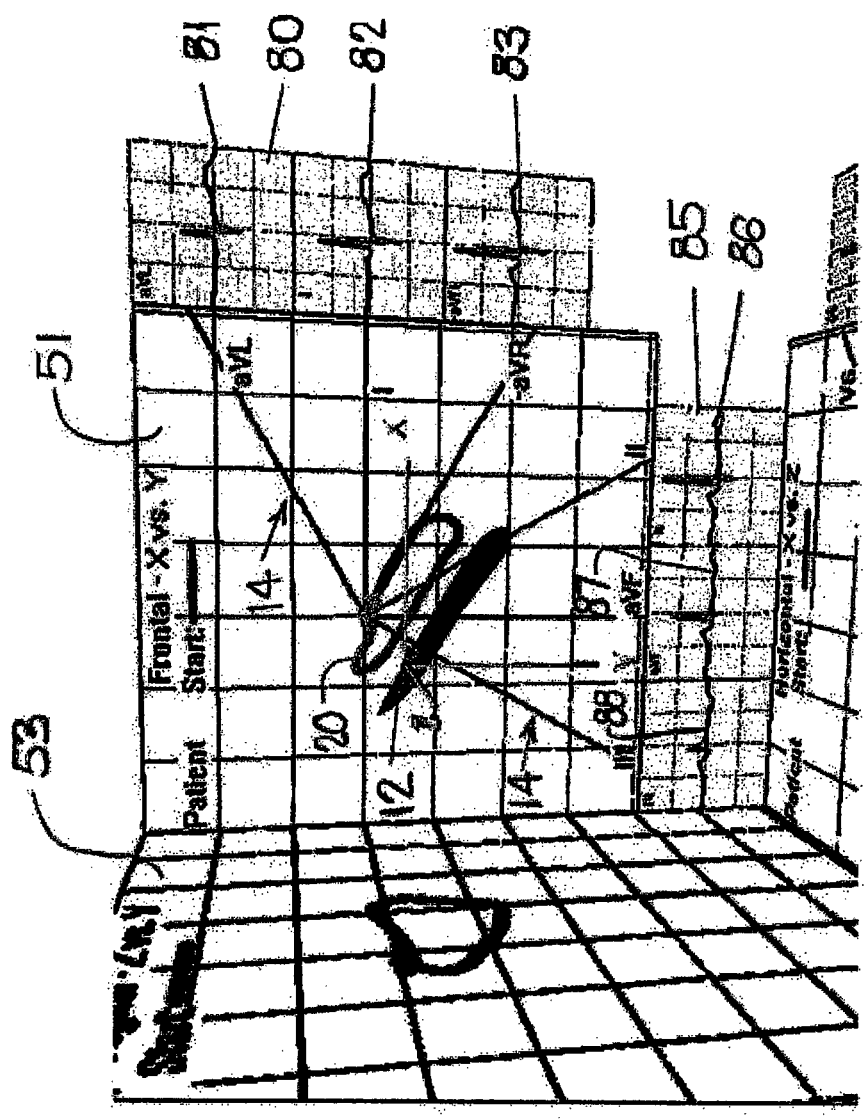
FIG. 11 illustrates a frontal view of a patient having a normal heart with the projections of the vectors onto the lead vectors being displayed.

FIG. 11 illustrates a frontal view of a patient having a normal heart with the projections of the vectors 20 onto the lead vectors 81, 82, 83 and 86, 87, 88 being displayed. The frontal view is obtained by selecting a symbol or marker, e.g., symbol 1090 or 'F' on the tool bar 100. The lead vectors 14 for each of the limb leads and the resultant projections 20 of the vectors are clearly shown in a frontal view.

Figure 12:
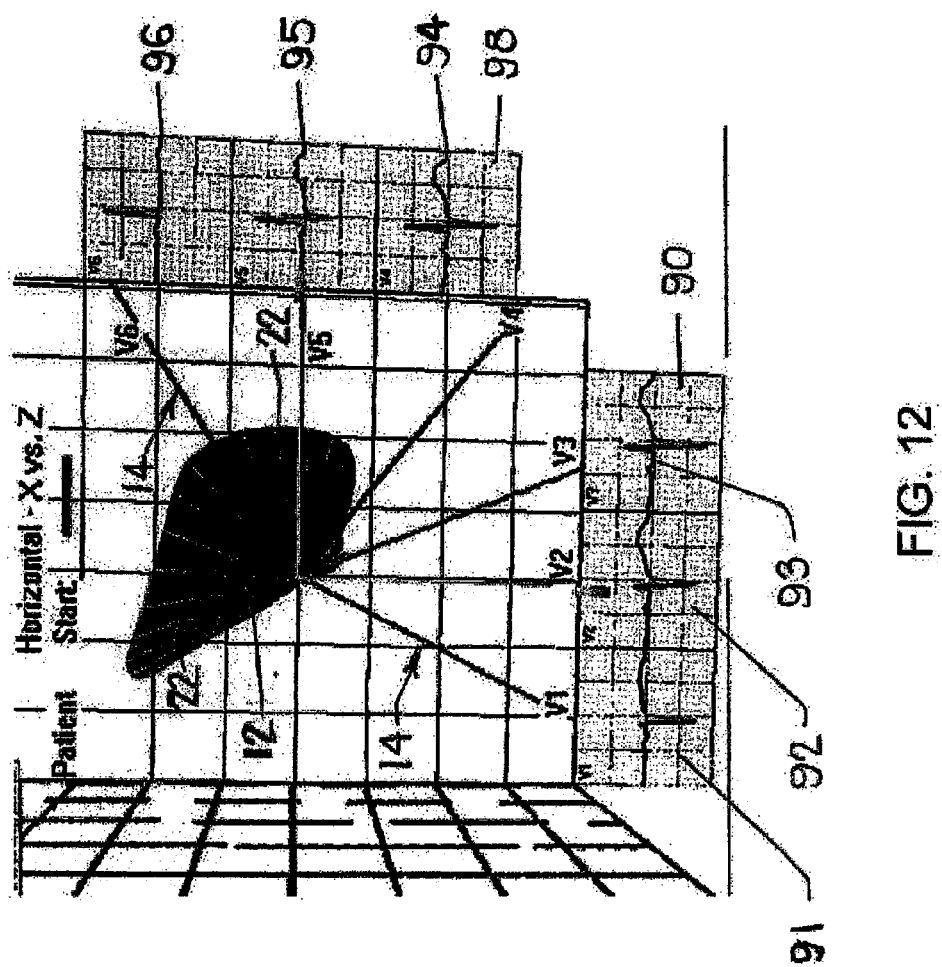
FIG. 12 illustrates a horizontal view of the patient having a normal heart with the projections of the vectors onto the lead vectors being displayed.

FIG. 12 illustrates a horizontal view of the patient having a normal heart with the projections of the vectors 22 onto the lead vectors 91, 92, 93 and 94, 95, 96 being displayed. The Horizontal display is obtained by selecting a symbol or marker, e.g., symbol 1100 or 'H' on the tool bar 100. As in the frontal view, the projections of the vectors 22 onto the lead vectors 14 is displayed.

Figure 13:
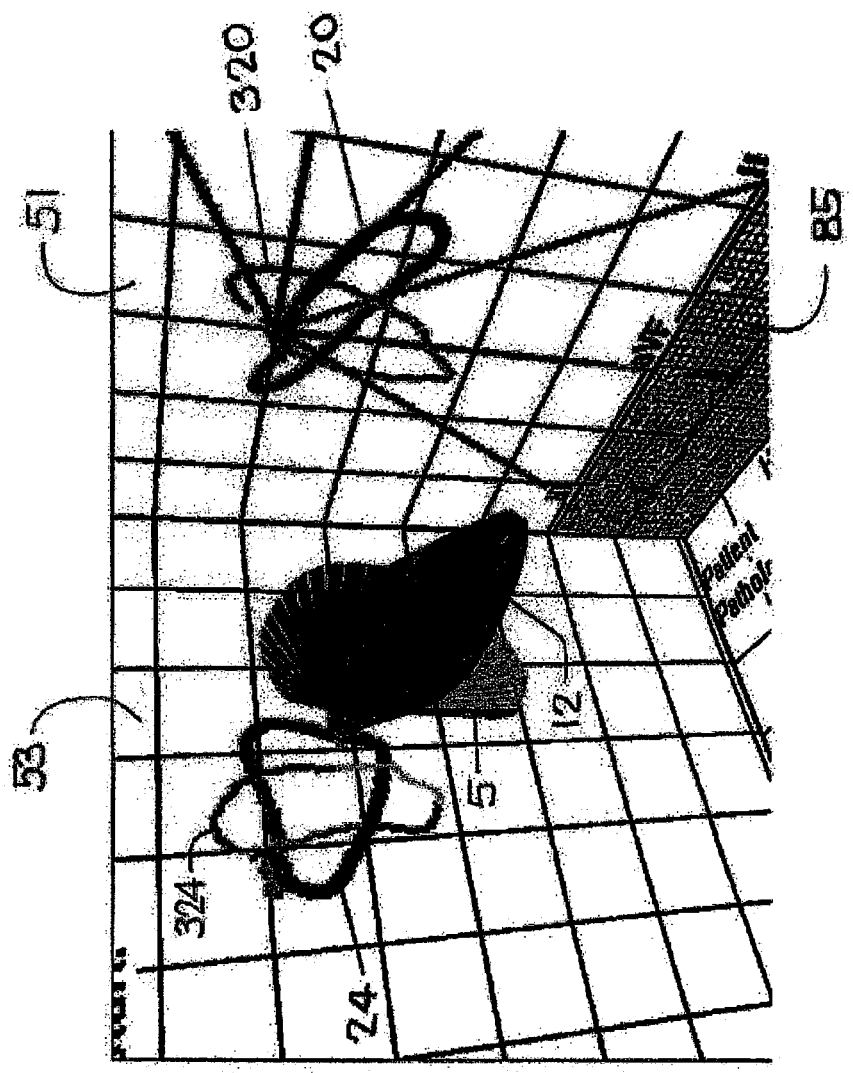
FIG. 13 illustrates the 3D vectorcardiograph of the patient in comparison with a large anterior myocardial infarction (MI)

FIG. 13 illustrates the 3D vectorcardiograph 12 of the normal patient of FIG. 1 in comparison with a large anterior myocardial infarction (MI) 126 (see FIG. 4B). The projections of the MI 126 onto the frontal and sagital planes 51 and 53 are illustrated as 320 and 324, respectively. The dramatic difference in the shape of these curves 320 and 324 as compared to the normal curves 20 and 24, respectively, makes recognition of the diagnosis of a large anterior MI quick and accurate.

The software allows the comparison of a current or prior 3D ECG 12 of a patient with any of the disease types 102 as shown on the tool bar menu 100. Therefore, recognition of the difference in two patterns, such as the normal pattern 12 compared to the large anterior MI 126, through the 3D presentation method of the present disclosure is greatly facilitated.

Figure 14:
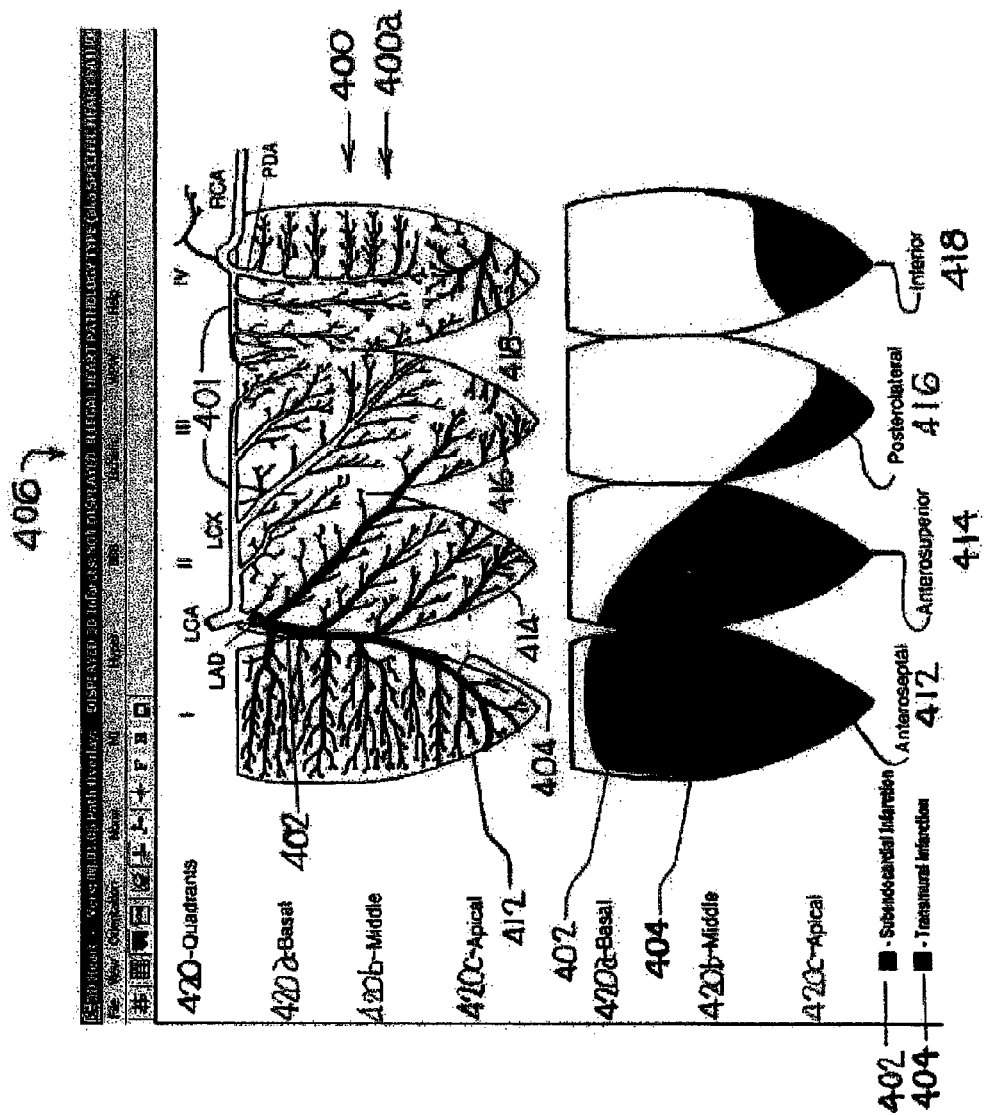
FIG. 14 illustrates a mercator projection of coronary arteries for two different levels of infarction conditions.

In FIG. 14, a display 406 displays a mercator projection of the left ventricle of the heart 5. This is advantageous for a user to diagnose what coronary arteries are blocked. In addition, the cardiac conditions 120 for myocardial infarctions (MI) (see FIG. 4B) can be displayed. A mercator projection 400 of coronary arteries 401 for two different levels of myocardial infarctions is illustrated: a subendocardial infarction 402 shown in blue and a transmural infarction 404 shown in black. By clicking on the symbol or icon 1030 as shown above and in FIG. 4A, a display 406 of the mercator projection 400 of the coronary arteries 401 is shown for the blockage type indicated. An upper display 400a illustrates the specific locations in the arteries 401 in which the infarctions have occurred. A lower display 400b illustrates the degree of infarction. The mercator projection displays 400a and 400b are divided into an anteroseptal projection 412, an anterosuperior 414, a posterolateral 416, and an interior 418. The display 406 also provides information regarding quadrants 420: the basal 420a, the middle 420b and the apical 420c. The projections 400a and 400b identify the parts of the myocardium that are damaged when this disease is present. In effect, the display 406 displays an overlay of the picture of coronary arteries 401 as a mercator projection 400 of a heart.

Figure 15:
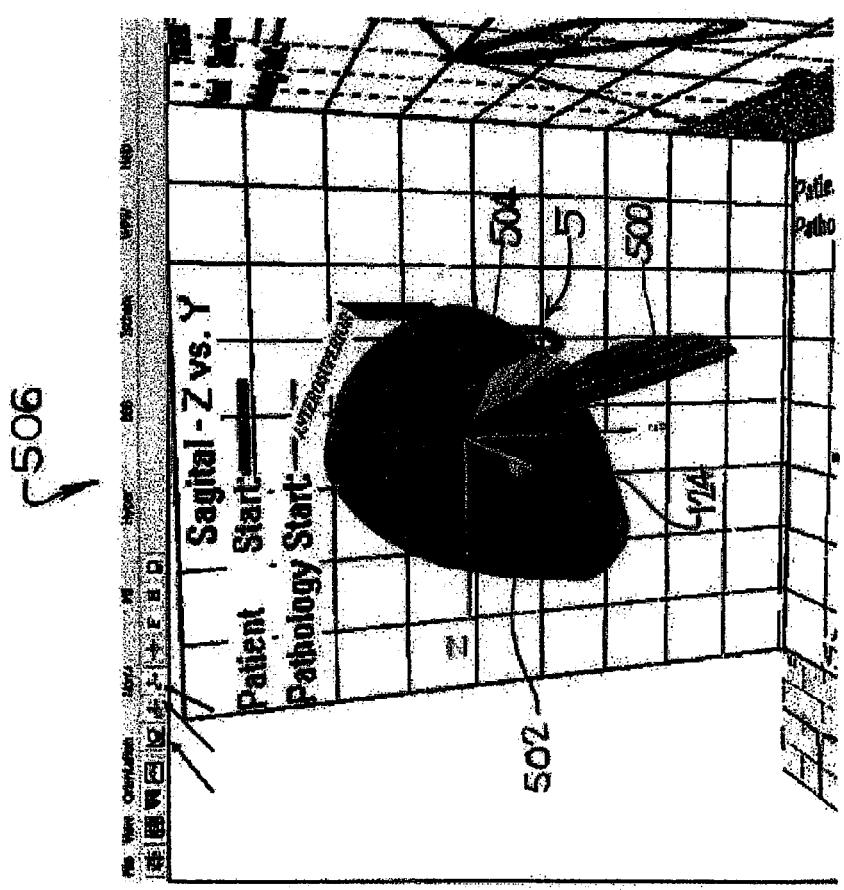
FIG. 15 illustrates a 3D vectorcardiograph of a patient having a medium anterior MI with a dark gray area representing those regions of the heart that are infarcted.

FIG. 15 illustrates a display 506 of a 3D vectorcardiograph 500 of the left ventricle 502 of a patient having a medium anterior MI 124a with a dark gray area 504 representing those regions of the left ventricle 502 that are infarcted. The origin of the vector diagram is positioned at the electrical center of the heart 5. The electrical center is defined as the center and is the origin of the vectorcardiograph 500. The 3D vectors represent the sum of the electrical activity of the myocardium which may be projected from the electrical center. A comparison with the stored version of a medium anterior MI 124 (see FIG. 4B) has been selected as well as the three axes X, Y and Z, and an overlay of the Left Ventricle 502 of the heart. The overlay is activated by selecting the icon 1050 on the display tool bar 400b (see FIG. 4B). The dark gray area 504 of the left ventricle 502 indicates those regions of muscle tissue that are infarcted. The dark regions of the heart 502 that are infarcted do not produce an electrical signal in the anterior direction along the Z axis. As a result, the active sections are mostly posterior and thus make the vectors point primarily in the inferior and posterior direction along the negative Z direction and in the Y direction. In this view, the patient signal looks green and the typical medium anterior MI signal is shown in yellow and green. By rotating the picture, i.e., the 3D vectorcardiograph 500, the total vector diagram can be seen with all the appropriate colors. Thus, recognition of the pattern of the 3D vectors that result is facilitated. This demonstrates quite dramatically the advantages of the 3D vectorcardiogram and its relation to the heart itself.

Figure 16:
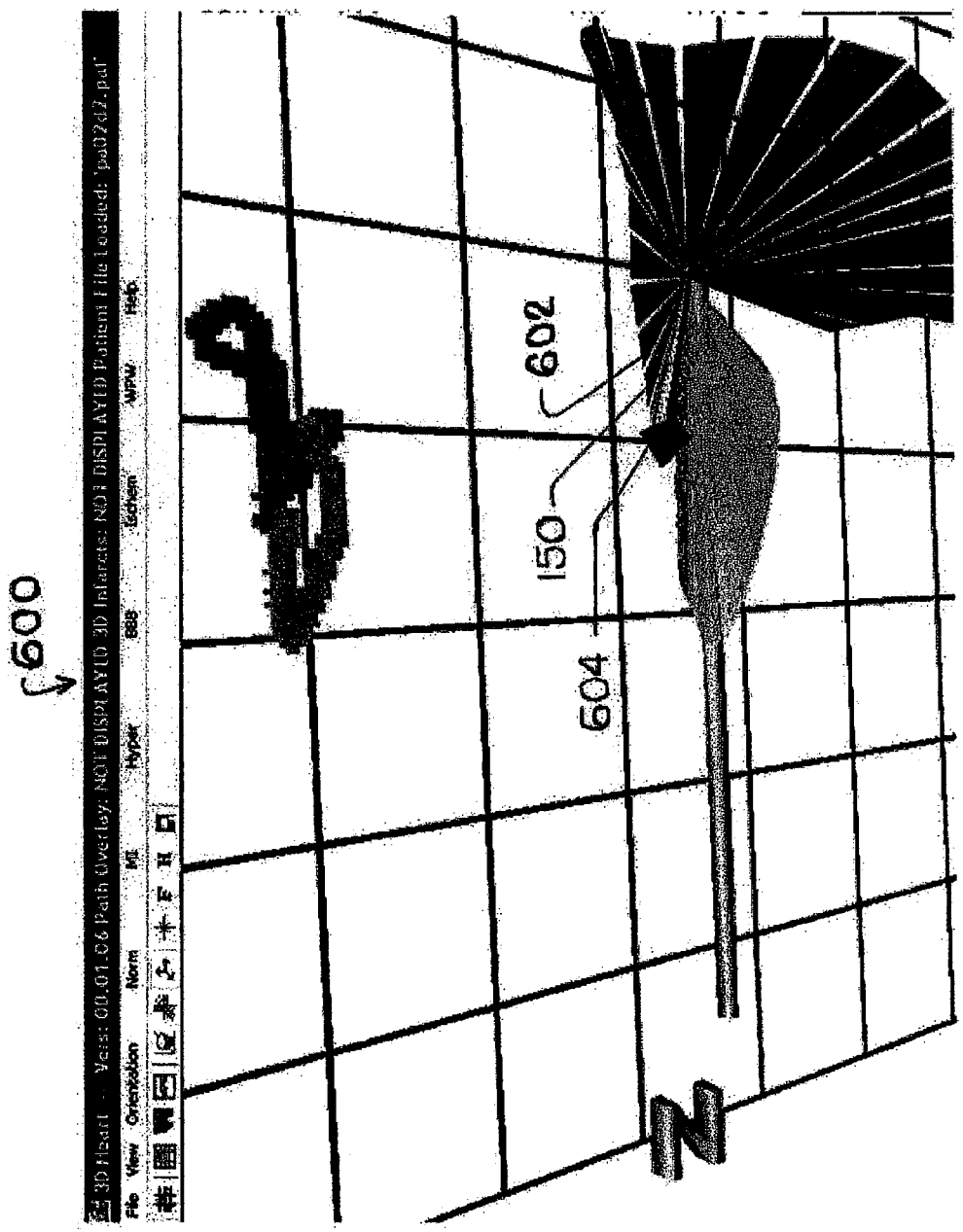
FIG. 16 illustrates a 3D vectorcardiograph of a patient having an ischemic condition represented by a vector.

FIG. 16 illustrates a display 600 of a 3D vectorcardiograph 602 of an ischemic condition 150 (see FIG. 4B) in which the direction of vector 604 clearly indicates the location of the ischemic condition 150 The vector 604 indicating the ischemic condition 150 is drawn at a location in the time sequence that is shortly after the end of the QRS cycle (J-point). The vector 604 is positioned at the J-point plus 60 ms, which is generally recognized to be sensitive to the effects of ischemia. By positioning a vector such as vector 604 at the J-point that is plainly visible, the presence of an ischemic condition may become essentially immediately apparent. The location of the ischemic condition 150 also becomes essentially immediately apparent with respect to the X, Y and Z coordinates, since the vector 604 points toward the area of the heart 5 (see FIG. 1) in which the ischemic condition 150 has occurred. As discussed below with respect to FIG. 19, the area in which the ischemic condition 150 has occurred is found by overlaying a 3D image of the Left Ventricle with the coronary arteries.

Figure 17:
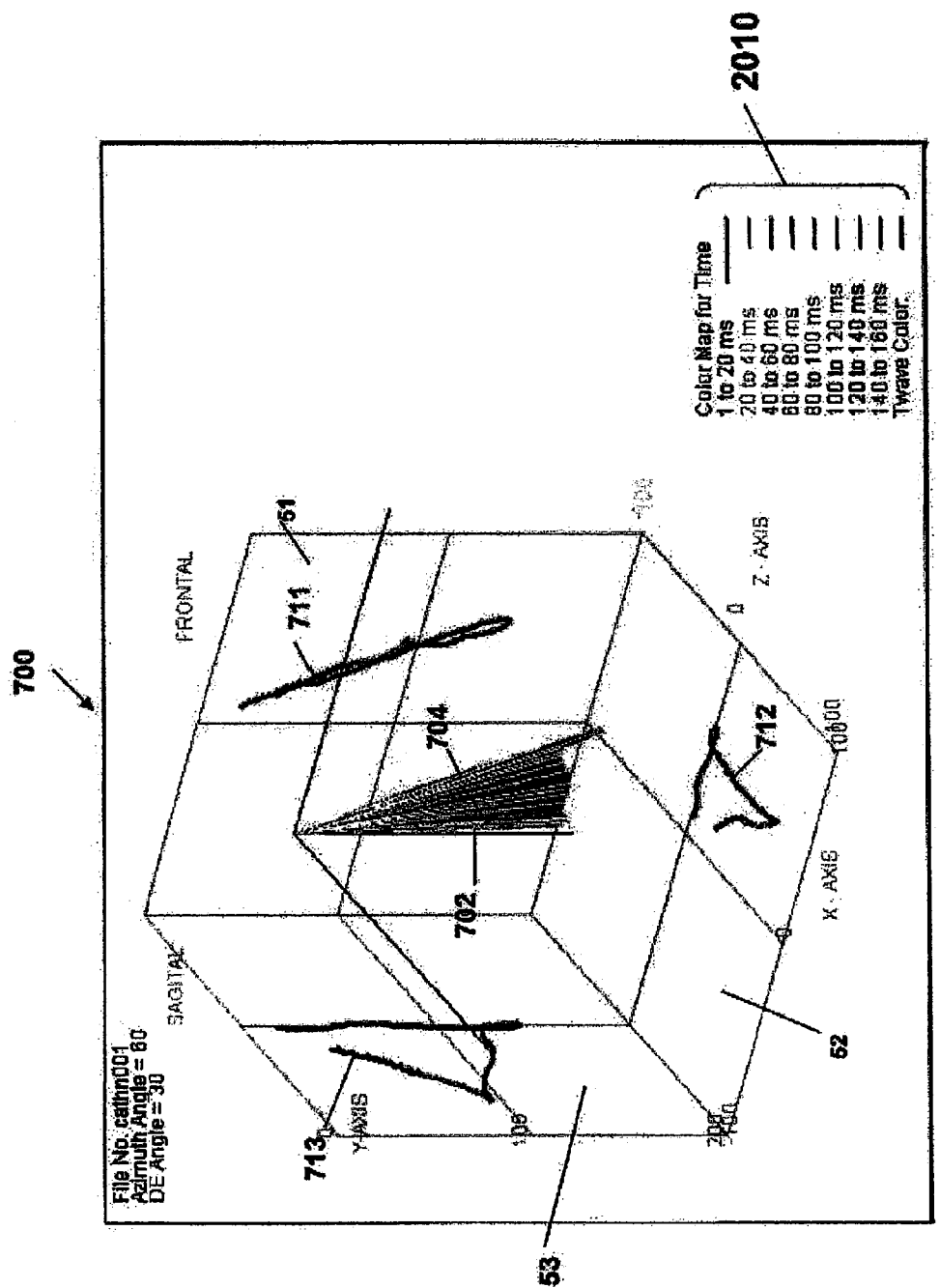
FIG. 17 illustrates a 3D vectorcardiograph of the normal P Wave segment of an ECG signal.

FIG. 17 illustrates a display 700 of a 3D vectorcardiograph 702 of a normal P-wave. A color map 2010, which is scaled at time sequences 2020 of about 20 milliseconds (ms) each is the same as for a QRS complex, as previously described with respect to FIGS. 1, 2, 8-12, and 15-16, since the time scale is about the same. The normal maximum amplitude 704 of the P-wave is between about 100 and about 200 microvolts, for the example as indicated on the X, Y and Z axes defining the frontal, horizontal and sagital planes 51, 52 and 53, respectively. The 3D vectorgraph 702 is projected as first planar projections or vector loops 711, 712 and 713, projected as time sequences, in color-coded form, onto frontal plane 51, horizontal plane 52, and sagital plane 53, respectively. The beginning vectors of vector loops 711, 712 or 713, color coded as black and blue, of the P-wave are associated with the Right Atrium. The latter part of the wave form and latter vectors of vector loops 711, 712 or 713, color coded as purple and green, relate to the Left Atrium. This 3D vectorcardiograph display 700 may form the main display of FIG. 1 and the surrounding panel displays 80, 85, 90, and 98, and the rhythm strip 60, the fiducial points 70, probable patient diagnosis 30, and the statistics of critical measurements 66 may be associated with the properties of the P-wave 3D vectorcardiograph 702.

Figure 18:
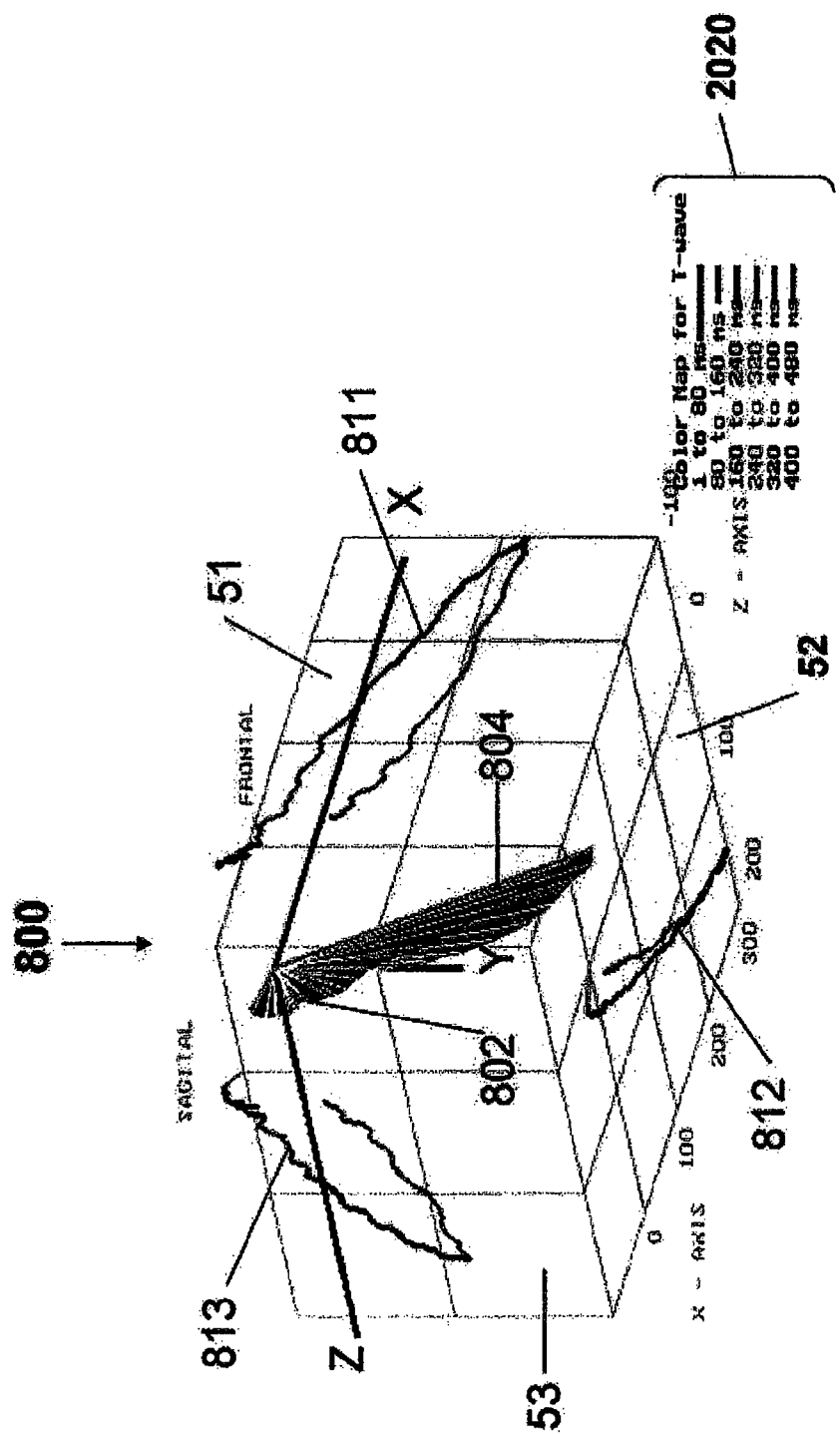
FIG. 18 illustrates a 3D vectorcardiograph of the normal T wave segment of an ECG signal.

FIG. 18 illustrates a display 800 of a 3D vectorcardiograph 802 of a normal T-wave. As compared to color map 2010 with respect to FIG. 17, a color map 2020 for this display is expanded to 80 ms per color, since the time scale is much longer for the T-wave than the QRS. The normal maximum amplitude of the T-wave signal 802 is scaled as necessary to effectively show the signal strength with a value of about 300 microvolts shown for illustrative purposes only, as indicated on the X, Y and Z axes defining the frontal, horizontal and sagital planes 51, 52, and 53, respectively. The 3D vectorgraph 802 is projected as first planar projections or vector loops 811, 812 and 813, projected as time sequences, in color-coded form, onto frontal plane 51, horizontal plane 52, and sagital plane 53, respectively. The normal direction for the T-wave is anterior and inferior, with a fairly narrow displacement about the maximum vector 804. In a similar manner as with respect to the P-wave described above with respect to FIG. 17, the 3D vectorcardiograph display 800 may form the main display of FIG. 1 and the surrounding panel displays 80, 85, 90, and 98, and the rhythm strip 60, the fiducial points 70, probable patient diagnosis 30, and the statistics of critical measurements 66 may be associated with the properties of the T-wave vectorcardiograph 802.

In FIGS. 1, 2, 3, 8, 9, 10, 11, 12, 13, 15, 16, 17, and 18 the cardiographic display 10 operatively communicates with the CPU 82 to implement a diagnostic algorithm 88 (see FIG. 3) to permit a user to selectively and visually convert and display the segment of the patient ECG signal 12 into a color coded projection of a time sequence with planar projections or vector loops 20, 22 and 24 projected as time sequences, in color-coded form, into the three planes: Frontal 51, Horizontal 52 and Sagital 53, respectively, as at least first color-coded projections. The color coded projections 20, 22 and 24 correspond to a magnitude and location of the vectorcardiograph signal 12. The first color-coded sequences 20, 22 and 24 represent a time line duration of the vectorcardiograph signal 12. The first color-coded frontal planar projection or vector loop 20 and 22 in turn may be projected into lead projections as corresponding second color-coded time sequence projections 81, 82, 83 and 86, 87, 88 associated with vector loop 20 and corresponding second color-coded time sequence projections 91, 92, 93 and 94, 95 and 96 associated with vector loop 22.

In conjunction with FIGS. 14 and 15, FIG. 19 illustrates a 3D display 900 of the coronary arteries 401 (see FIG. 14) of a 3D heart 501 as the arteries 401 are associated with the Left Ventricle 501 of the heart 501. The 3D display 900 may be situated at the origin of the X, Y, Z axes (see FIG. 15) and may be made semi-transparent so that the 3D vectorgram or vectorcardiograph of the ECG signal 12 may project through an outer shell or periphery 506 of the heart 501 as illustrated in FIG. 15. Thus, the effects of MI 120 or ischemia 150 (see FIG. 4B) may be associated with the appropriate area of coronary arteries 401 causing the disease state being observed.

As can be appreciated from the foregoing, FIGS. 1-19 present the medical display 10 for analyzing heart signals that includes the cardiographic display 10 which displays an electrocardiograph (ECG) heart signal 12 of a patient having a magnitude and location in vector format 14 within a single three-dimensional (3D) coordinate system, e.g., X, Y, Z, (vectorcardiograph) sampled at incremental time intervals. The display 10 operatively communicates with the CPU 82 that implements a diagnostic algorithm 88 to permit a user to selectively and visually display a comparison 90 of the patient ECG with at least one known display 102 in vector format within a single three-dimensional (3D) coordinate system. The known display(s) consist of a normal cardiac condition 110 (including a patient's prior or current normal condition) or an abnormal or reference cardiac condition that includes at least one of a patient prior or current cardiac condition, a myocardial infarction condition 120, a hypertrophic condition 140, an ischemic condition 150, and a bundle branch block condition 190. The known displays 102 in vector format are stored in the known cardiac conditions database 86, which in turn is stored in the memory 84. (See FIGS. 3 and 4A-4B).

The cardiographic display 10 may operatively communicate with the CPU 82 to allow a user to selectively display critical measurements 66 of at least one of the patient ECG 12, obtained via the patient monitoring 74, and the known display(s) 102 in vector format.

The algorithm 88 may compare the patient ECG critical measurements 66 to the critical measurements stored in the cardiac conditions database 86 and the CPU 82 may operatively communicate with the cardiographic display 10 to visually display the results of the comparison 90 as a normal or abnormal condition. In addition, the cardiographic display 10 may operatively communicate with the CPU 82 to allow a user to selectively display an overlay over the vectorcardiograph patient ECG 12, with the overlay including at least one of a 3D representation of a heart 5, a representation of coronary arteries 400 over a projection of a heart, and a 3D vectorcardiograph 12 of a cardiac condition 102. Also, the segment of patient ECG signal 72 may include at least one of a P-wave interval, PR interval, QRS interval, QT interval and T-wave interval (see FIG. 6).

Referring again to FIGS. 1-19, it can be appreciated also that the present disclosure relates to a method for analyzing heart signals, which includes the step of implementing the algorithm 88 to permit a user to selectively and visually display a comparison of the electrocardiograph (ECG) heart signal 12 of a patient having a magnitude and location in vector format within a single three-dimensional (3D) coordinate system (vectorcardiograph) sampled at incremental time intervals with at least one known display 102 in vector format within a single three-dimensional (3D) coordinate system. The known display(s) consist of a normal cardiac condition 110 (including a patient's prior or current normal condition) or an abnormal or reference cardiac condition that includes at least one of a patient prior or current cardiac condition, a myocardial infarction condition 120, a hypertrophic condition 140, an ischemic condition 150, and a bundle branch block condition 190. As previously indicated, the known displays 102 in vector format are stored in the known cardiac conditions database 86, which in turn is stored in the memory 84. (See FIGS. 3 and 4A-4B).

The step of implementing the algorithm 88 may further include implementing the algorithm to allow the user to selectively display the critical measurements 66 of at least one of the segment of patient ECG 12 signal and the known display in vector format 102. The step of implementing the algorithm further may also include implementing the algorithm 88 to allow a user to compare the patient ECG critical measurements 66 to critical measurements 86 stored in a database and to operatively communicate with the cardiographic display 10 to visually display the results as a normal or abnormal condition. The step of implementing the algorithm may further include implementing the algorithm 88 to allow a user to selectively display an overlay over the vectorcardiograph patient ECG 12. The overlay includes at least one of a 3D representation of a heart 5, a representation of coronary arteries 400 over a projection of a heart, and a 3D vectorcardiograph 12 of a cardiac condition 102. The segment of the patient ECG signal 12 may include at least one of a P-wave interval, PR interval, QRS interval, QT interval and T-wave interval (72 in FIG. 6).

The present disclosure relates also to a method of displaying the electrocardiograph (ECG) heart signal 12 having a magnitude and location in vector format within a single three-dimensional (3D) coordinate system (e.g., X Y Z) sampled at incremental time intervals, which includes implementing the steps of displaying the cardiac conditions 102 and separating the cardiac conditions 102 into recognizable patterns of 3D vectors 14.

Referring to FIGS. 1-3, the method may include displaying the critical measurements 66 of at least one of the recognizable patterns of 3D vectors 14 and comparing the display of critical measurements 66 to statistical information for at least one of the cardiac conditions 102. The cardiac condition may be a normal condition 110 or an abnormality such as, but not limited to, MI 120, hypertrophy 140, ischemia 150, or BBB 190 and their sub-categories.

As illustrated in FIGS. 7-12, the method may include the step of displaying the heart signal 12 in X, Y and Z vector signals 14 and the resultant magnitude of the signal $Mag_{vd}=\sqrt{(x^2+y^2+z^2)}$, as previously described. Alternatively, other 3D coordinate systems such as cylindrical coordinates may be implemented to perform the method. The embodiments are not limited in this context. The method may include utilizing the X, Y and Z vector signals 14 and the resultant magnitude of the signal $Mag_{vd}$ to illustrate an estimate of at least the P-wave interval, or the PR interval, or the QRS interval, or the QT interval or the T-wave interval. FIGS. 7-12 also illustrate that the method may include displaying an overlay of a 3D picture of a heart 5 over the 3D vectorcardiograph 12.

Alternatively, or in addition thereto, as also illustrated in FIG. 14, the method may include the step of displaying an overlay of a 3D ECG of a cardiac condition, e.g., MI 126, over the 3D ECG of the patient 12. As illustrated in, and described above with respect to, FIGS. 15 and 19, the method may include displaying an overlay of a picture of coronary arteries 401 over a 3D projection of a heart 501. As can be appreciated, the present disclosure relates to a 3D cardiographic display and method based on software tools to enhance diagnostic presentation of ECG data. The cardiographic display and the method of presentation separate the various heart abnormalities into easily recognizable patterns of 3D vectors. The software provides a comprehensive "menu" of diagnostic and treatment decision support tools. The support tools may include:

Comparison of the patient 3D display with known patterns for a selected abnormality.

Previous ECGs from that patient and their patterns.

Critical measurements of the 3D pattern and comparison with statistical information for known abnormalities providing Z scores.

A rhythm strip to show any abnormalities in this venue.

The presentation of one heart cycle showing X, Y, and Z signals and their resultant magnitude for the best estimates of P-wave Duration, PR interval, QRS duration, and QT interval.

The ability to overlay the 3D picture of the heart on top of the 3D vectorcardiogram to identify areas of disease such as MI and ischemia.

The ability to overlay the picture of the coronary arteries on top of the heart to locate the region of ischemia in 3D or as a mercator projection.

While the above description contains many specifics, these specifics should not be construed as limitations on the scope of the present invention, but merely as exemplifications of particular embodiments thereof. Those skilled in the art will envision many other possible variations that are within the scope and spirit of the present invention.

What is claimed is:

1. A medical display for analyzing heart signals, comprising:
    a cardiographic display which displays at least a segment of an electrocardiograph (ECG) heart signal of a patient having a magnitude and location in vector format within a single three-dimensional (3D) coordinate system (vectorcardiograph) sampled at incremental time intervals, said display operatively communicating with a central processing unit (CPU) that implements an algorithm to permit a user to selectively and visually display a comparison of at least one critical measurement of the at least a segment of the patient ECG with at least one known display of at least one corresponding critical measurement in vector format within a single three-dimensional (3D) coordinate system selected from the group consisting of at least a segment of a normal cardiac condition and at least a segment of an abnormal cardiac condition, the at least one corresponding critical measurement being at least one of a narrowness of width of the 3D vectorgraph compared to the measurement of the QRS amplitude, initial azimuth angle or initial elevation angle and/or combinations thereof.

2. A medical display according to claim 1, wherein the abnormal cardiac condition includes at least one of a patient prior cardiac condition, a myocardial infarction condition, a hypertrophic condition, an ischemic condition and a bundle branch block condition.

3. A medical display according to claim 1, wherein the algorithm compares the at least one patient ECG critical measurement to at least one corresponding critical measurement stored in a cardiac conditions database and the CPU operatively communicates with the cardiographic display to visually display the results of the comparison as one of a normal condition and abnormal condition.

4. A medical display according to claim 1, wherein said cardiographic display operatively communicates with the CPU to allow a user to selectively display an overlay over the vectorcardiograph patient ECG, said overlay including at least one of a 3D representation of a heart, a representation of coronary arteries, and a 3D vectorcardiograph of a cardiac condition.

5. A medical display according to claim 1, wherein the at least a segment of an ECG signal includes at least one of a P-wave interval, PR interval, QRS interval, QT interval and T-wave interval.

6. A medical display according to claim 1, wherein the medical display comprises:
    a cardiographic display which displays at least a QRS segment of an electrocardiograph (ECG) heart signal of a patient having a magnitude and location in vector format within a single three-dimensional (3D) coordinate system (vectorcardiograph) sampled at incremental time intervals, said display operatively communicating with a central processing unit (CPU) that implements an algorithm to permit a user to selectively and visually display a comparison of a flat plane of vectors spaced apart to show continuity of generation, smoothness of timing, planarity, and shape of the QRS pattern and at least one critical measurement of the at least a corresponding QRS segment of the patient ECG with at least one known display of at least one corresponding critical measurement in vector format within a single three-dimensional (3D) coordinate system selected from the group consisting of at least a QRS segment of a normal cardiac condition and at least a QRS segment of an abnormal cardiac condition, the at least one critical measurement being at least one of a narrowness of width of the 3D vectorgraph compared to the measurement of the QRS amplitude, initial azimuth angle or initial elevation angle and/or combinations thereof.

7. A medical display according to claim 6, wherein the at least one critical measurement is at least one of a narrowness of width of the 3D vectorgraph compared to the measurement of the QRS amplitude, initial azimuth angle or initial elevation angle and/or combinations thereof and at least one of a maximum QRS amplitude, QRS duration, azimuth angle at maximum, elevation angle at maximum, T-wave maximum amplitude, T-wave azimuth angle at maximum or T-wave elevation angle at maximum and/or combinations thereof.

8. A medical display according to claim 1, wherein the at least one critical measurement is at least one of a narrowness of width of the 3D vectorgraph compared to the measurement of the QRS amplitude, initial azimuth angle or initial elevation angle and/or combinations thereof and at least one of a maximum QRS amplitude, QRS duration, azimuth angle at maximum, elevation angle at maximum, T-wave maximum amplitude, T-wave azimuth angle at maximum or T-wave elevation angle at maximum and/or combinations thereof.

9. A method for analyzing heart signals, comprising the step of:
    implementing an algorithm to permit a user to selectively and visually display a comparison of at least one critical measurement of at least a segment of an electrocardiograph (ECG) heart signal of a patient having a magnitude and location in vector format within a single three-dimensional (3D) coordinate system (vectorcardiograph) sampled at incremental time intervals with at least one known display of at least one corresponding critical measurement in vector format within a single three-dimensional (3D) coordinate system selected from the group consisting of a normal cardiac condition and an abnormal condition, the at least one corresponding critical measurement being at least one of a combination of narrowness of width of the 3D vectorgraph compared to the measurement of the QRS amplitude, initial azimuth angle, or initial elevation angle and/or combinations thereof.

10. A method according to claim 9, wherein the abnormal cardiac condition includes at least one of a patient cardiac condition, a myocardial infarction condition, a hypertrophic condition, an ischemic condition and a bundle branch block condition.

11. A method according to claim 9, wherein the step of implementing the algorithm further comprises
    implementing the algorithm to allow a user to compare the at least one patient ECG critical measurement to at least one corresponding critical measurement stored in a database and to operatively communicate with the cardiographic display to visually display the results as a normal or abnormal condition.

12. A method according to claim 11, wherein the step of implementing the algorithm further comprises
implementing the algorithm to allow a user to selectively display an overlay over the vectorcardiograph patient ECG, said overlay including at least one of a 3D representation of a heart, a representation of coronary arteries over a projection of a heart, and a 3D vectorcardiograph of a cardiac condition.

13. A method according to claim 9, wherein the at least a segment of an ECG signal includes at least one of a P-wave interval, PR interval, QRS interval, QT interval and T-wave interval.

14. A method according to claim 9, wherein the at least one critical measurement is at least one of a narrowness of width of the 3D vectorgraph compared to the measurement of the QRS amplitude, initial azimuth angle or initial elevation angle and/or combinations thereof and at least one of a maximum QRS amplitude, QRS duration, azimuth angle at maximum, elevation angle at maximum, T-wave maximum amplitude, T-wave azimuth angle at maximum or T-wave elevation angle at maximum and/or combinations thereof.

15. A method for analyzing heart signals, comprising the steps of:
implementing an algorithm to permit a user to selectively and visually display at least a segment of an electrocardiograph (ECG) heart signal of a patient having a magnitude and location in vector format within a single three-dimensional (3D) coordinate system (vectorcardiograph) sampled at incremental time intervals; and
implementing the algorithm to allow a user to selectively display an overlay of an average of vector characteristics of patients having a normal or abnormal heart over the vectorcardiograph patient ECG.

16. The method for analyzing heart signals according to claim 15, wherein the step of implementing the algorithm to allow a user to selectively display an overlay of an average of vector characteristics of patients having a normal or abnormal heart over the vectorcardiograph patient ECG is performed by implementing the algorithm to allow a user to selectively display an average of at least one of a narrowness of width of the 3D vectorgraph compared to the measurement of the QRS amplitude, initial azimuth angle or initial elevation angle and/or combinations thereof.

17. The method for analyzing heart signals according to claim 15, wherein the step of implementing an algorithm to permit a user to selectively and visually display at least a segment of an electrocardiograph (ECG) heart signal of a patient is performed by implementing the algorithm to permit a user to selectively and visually display at least a segment of an electrocardiograph (ECG) heart signal of a patient having a magnitude and location in vector format within a single three-dimensional (3D) coordinate system (vectorcardiograph) sampled at incremental time intervals in one of the group consisting of in a three-dimensional image of the vector cardiograph or in a two-dimensional planar image of the vector cardiograph.

18. The method for analyzing heart signals according to claim 15, wherein the step of implementing the algorithm to allow a user to selectively display an overlay of an average of vector characteristics of patients having a normal heart over the vectorcardiograph patient ECG is performed by implementing the algorithm to allow a user to selectively display an overlay of an average of vector characteristics of patients having a normal or abnormal heart over the vectorcardiograph patient ECG in either a three-dimensional image of the vector cardiograph or in a two-dimensional planar image of the vector cardiograph.

19. A method according to claim 15, wherein the step of implementing the algorithm to allow a user to selectively display an overlay of an average of vector characteristics of patients having a normal or abnormal heart over the vectorcardiograph patient ECG is performed by implementing the algorithm to allow a user to selectively display an average of at least one of a narrowness of width of the 3D vectorgraph compared to the measurement of the QRS amplitude, initial azimuth angle or initial elevation angle and/or combinations thereof and at least one of a maximum QRS amplitude, QRS duration, azimuth angle at maximum, elevation angle at maximum, T-wave maximum amplitude, T-wave azimuth angle at maximum or T-wave elevation angle at maximum and/or combinations thereof.

20. A medical display for analyzing heart signals, comprising:
a cardiographic display which displays at least a segment of an electrocardiograph (ECG) heart signal of a patient having a magnitude and location in vector format within a single three-dimensional (3D) coordinate system (vectorcardiograph) sampled at incremental time intervals, said display operatively communicating with a central processing unit (CPU) that implements an algorithm to permit a user to selectively and visually display at least a segment of an electrocardiograph (ECG) heart signal of a patient having a magnitude and location in vector format within a single three-dimensional (3D) coordinate system (vectorcardiograph) sampled at incremental time intervals and to permit a user to selectively display an overlay of an average of vector characteristics of patients having a normal or abnormal heart over the vectorcardiograph patient ECG.

21. A medical display according to claim 20, wherein the critical parameters are at least one of a narrowness of width of the 3D vectorgraph compared to the measurement of the QRS amplitude, initial azimuth angle or initial elevation angle and/or combinations thereof.

22. A medical display according to claim 21, wherein the critical parameters are at least one of a narrowness of width of the 3D vectorgraph compared to the measurement of the QRS amplitude, initial azimuth angle or initial elevation angle and/or combinations thereof and at least one of a maximum QRS amplitude, QRS duration, azimuth angle at maximum, elevation angle at maximum, T-wave maximum amplitude, T-wave azimuth angle at maximum or T-wave elevation angle at maximum and/or combinations thereof.

23. A medical display according to claim 20, wherein said cardiographic display operatively communicates with the CPU to allow a user to selectively and visually display the at least a segment of an electrocardiograph (ECG) heart signal of a patient having a magnitude and location in vector format within a single three-dimensional (3D) coordinate system (vectorcardiograph) sampled at incremental time intervals in either a three-dimensional image of the vector cardiograph or in a two-dimensional planar image of the vector cardiograph.

24. A medical display according to claim 20, wherein said cardiographic display communicates with the CPU to allow a user to selectively and visually display the overlay of an average of vector characteristics of patients having a normal or abnormal heart over the vectorcardiograph patient ECG in either a three-dimensional image of the vector cardiograph or in a two-dimensional planar image of the vector cardiograph.

* * * * *